United States Patent
Lam

(10) Patent No.: US 9,060,750 B2
(45) Date of Patent: Jun. 23, 2015

(54) PLASMA HEAD FOR TISSUE WELDING

(75) Inventor: Amnon Lam, Kibuz Givat Oz (IL)

(73) Assignee: IONMED LTD., Yokneam (IL)

( * ) Notice: Subject to any disclaimer, the term of this patent is extended or adjusted under 35 U.S.C. 154(b) by 383 days.

(21) Appl. No.: 13/508,950

(22) PCT Filed: Nov. 8, 2010

(86) PCT No.: PCT/IL2010/000922
§ 371 (c)(1),
(2), (4) Date: Jul. 25, 2012

(87) PCT Pub. No.: WO2011/055368
PCT Pub. Date: May 12, 2011

(65) Prior Publication Data
US 2012/0283732 A1 Nov. 8, 2012

Related U.S. Application Data

(60) Provisional application No. 61/259,324, filed on Nov. 9, 2009.

(51) Int. Cl.
| | | |
|---|---|---|
| *A61B 18/12* | (2006.01) | |
| *A61B 17/00* | (2006.01) | |
| *A61B 18/14* | (2006.01) | |
| *A61B 18/04* | (2006.01) | |

(52) U.S. Cl.
CPC ....... *A61B 17/00491* (2013.01); *A61B 18/1402* (2013.01); *A61B 18/042* (2013.01); *A61B 2017/00508* (2013.01); *A61B 2017/00517* (2013.01)

(58) Field of Classification Search
USPC ..................................... 606/41, 213
See application file for complete search history.

(56) References Cited

U.S. PATENT DOCUMENTS

| | | | |
|---|---|---|---|
| 5,669,934 A * | 9/1997 | Sawyer | 606/213 |
| 6,099,523 A | 8/2000 | Kim et al. | |
| 6,183,498 B1 | 2/2001 | Devore et al. | |
| 2003/0216729 A1 | 11/2003 | Marchitto et al. | |
| 2005/0011861 A1 | 1/2005 | Choo et al. | |
| 2007/0008045 A1 | 1/2007 | Camparo et al. | |
| 2008/0045941 A1 | 2/2008 | Fugo | |
| 2008/0183167 A1* | 7/2008 | Britva et al. | 606/41 |
| 2009/0099579 A1 | 4/2009 | Nentwick et al. | |

* cited by examiner

*Primary Examiner* — Carl H Layno
*Assistant Examiner* — Jon Eric C Morales
(74) *Attorney, Agent, or Firm* — Browdy and Neimark, PLLC

(57) ABSTRACT

A compact medical device for tissue welding is provided. The hand-held plasma heads are configured for deep cuts and long cuts. A bio-compatible liquid capable of solidifying in response to application of plasma, such as an albumin solution, is applied to the wound. Plasma created from a gas such as helium is then applied to said bio-compatible liquid to solidify it and seal the wound. An additional polymerizing gas may also be applied. A feedback mechanism may maintain the temperature of said plasma. A wiper fort removal of excess liquid may also be provided.

11 Claims, 26 Drawing Sheets

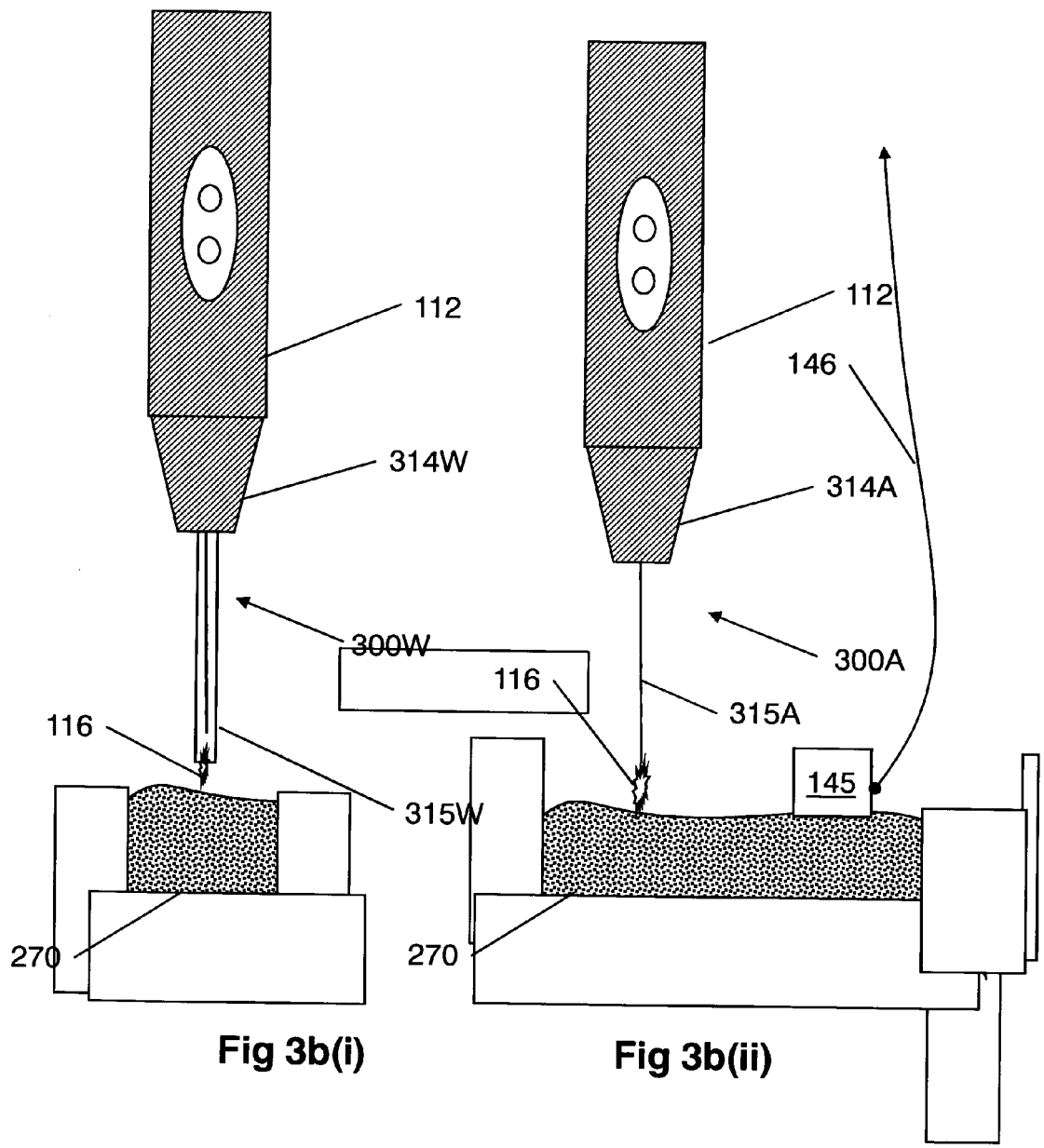
Fig 3b(i)        Fig 3b(ii)

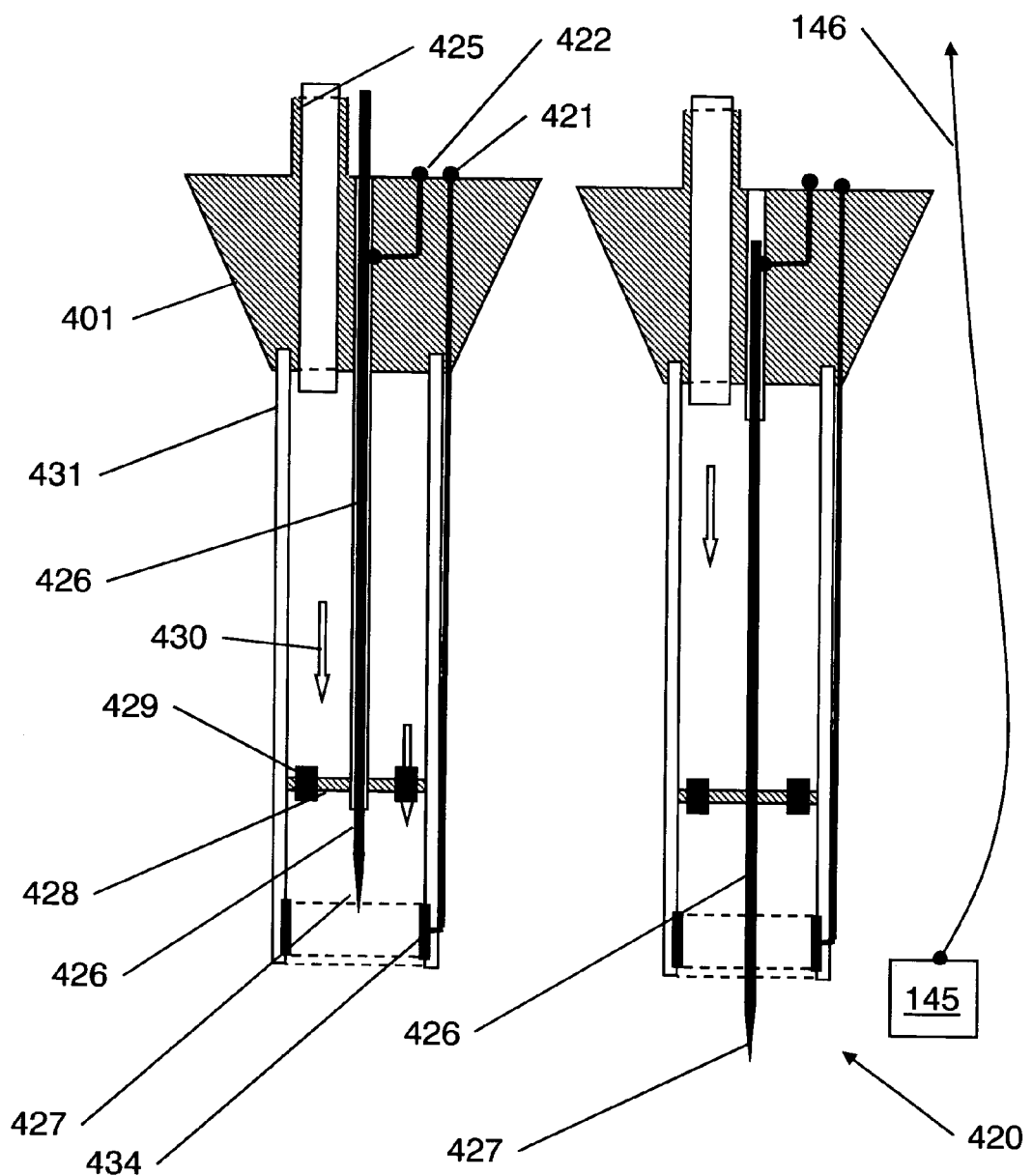
Fig 4b(i)  Fig 4b(ii)

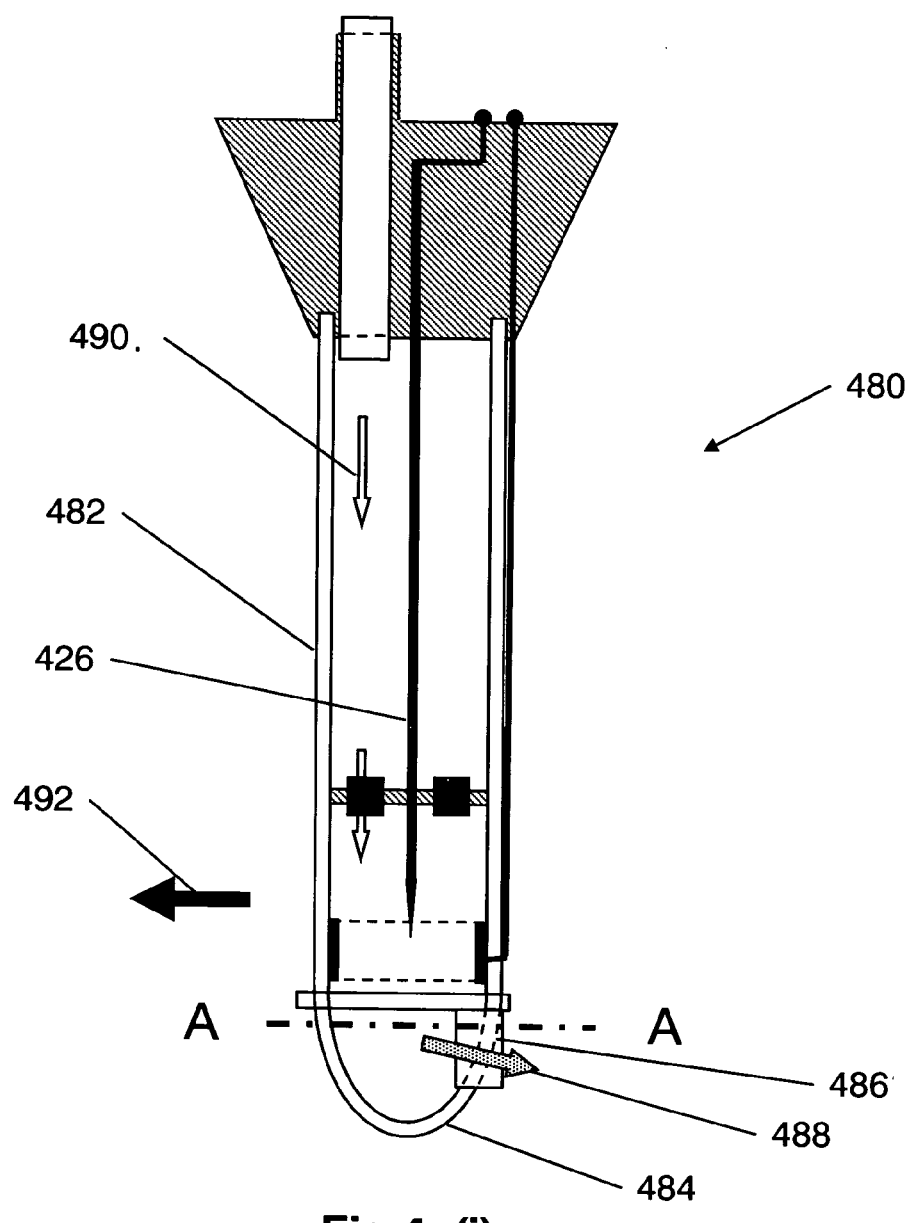
Fig 4e(i)
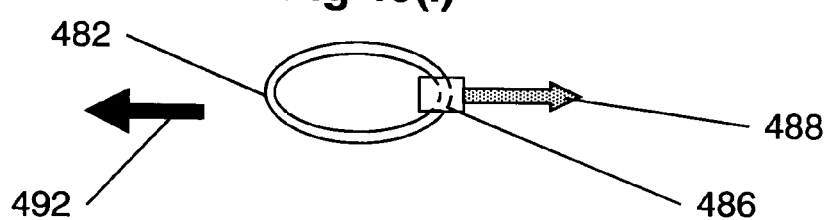
Fig 4e(ii)

PLASMA HEAD FOR TISSUE WELDING

FIELD OF THE INVENTION

The present invention relates to an apparatus and method for tissue welding using a plasma head.

BACKGROUND OF THE INVENTION

Traditional methods for closing tissue wounds or incisions include the use of glues, sutures, clips, or staples. While such techniques are generally adequate in sealing tissue wounds or incisions, they have associated problems that limit their use. For example, often lead to scar formation, infection, and a multitude of immunological responses. Tissue incompatibility with sutures, clips, or staples may cause fistulas, granulomas, and neuromas that can be painful and difficult to treat. Sutures, clips, or staples may also tend to cut through weak parenchymatous or poorly vascularized tissue. Additionally, sutures leave behind a tract that can allow for leakage of fluids and can provide a convenient entry point for a variety of organisms.

The success of traditional methods in sealing tissue wounds or incisions also is very dependent on the skill of the practitioner performing such methods, especially when microsurgery is being performed.

An alternative to traditional methods for sealing tissue wounds or incisions is the use of compositions suitable for tissue welding. By "tissue welding" it is meant that an energy source is used to excite the composition, which results in the sealing or closure of the tissue wound or incision. Typically, a tissue welding composition will be applied to the area of the tissue that requires sealing. Upon excitation by an energy source, the composition fuses to the tissue, and the bonding between the composition and the tissue allows the severed parts of the tissue to be proximal to each other, much in the same way as when sutures, staples, or clips are used. Such tissue welding compositions are absorbable within a few weeks and, therefore, do not cause tissue scar formation.

Numerous instruments are known which coagulate, seal, join, or cut tissue. Some of these devices may operate with a heating element in contact with the tissue, with an ultrasonic heater that employs frictional heating of the tissue, or with a mono- or bi-polar electrode heating system that passes current through the tissue such that the tissue is heated by virtue of its own electrical resistance.

Some devices heat the tissue to temperatures such that the tissue is either "cut" or "sealed", as follows. When tissue is heated in excess of 100° Celsius, the tissue will be broken down and is thus, "cut". However, when the tissue is heated to temperatures between 50° to 90° Celsius, the tissue will instead simply "seal" or "weld" to adjacent tissue. Numerous devices employing the same general principle of controlled application of a combination of heat and pressure can be used to join or "weld" adjacent tissues to produce a junction of tissues or an anastomosis of tubular tissues.

Mono-polar and bipolar probes, forceps or scissors use high frequency electrical current that passes through the tissue to be coagulated. The current passing through the tissue causes the tissue to be heated, resulting in coagulation of tissue proteins. In the mono-polar variety of these instruments, the current leaves the electrode and after passing through the tissue, returns to the generator by means of a "ground plate" which is attached or connected to a distant part of the patient's body. In a bipolar version of such an electrosurgical instrument, the electric current passes between two electrodes with the tissue being placed or held between the two electrodes.

There are many examples of such mono-polar and bipolar instruments commercially available today from companies including Valley Lab, Cabot, Meditron, Wolf, Storz and others worldwide.

In ultrasonic tissue heaters, a very high frequency (ultrasonic) vibrating element or rod is held in contact with the tissue. The rapid vibrations generate heat causing the proteins in the tissue to become coagulated.

Applying electrically generated plasma to medical application is known in the art.

For example, electrosurgery surgery is known in the art and is performed by electrical methods. Its development has been driven by the clinical need to control bleeding during surgical procedures. While heat has been used medically to control bleeding for thousands of years, the use of electricity to produce heat in tissue has only been in general use since the mid 1920's, and in flexible endoscopy since the 1970's. Electrosurgery offers at least one unique advantage over mechanical cutting and thermal application: the ability to cut and coagulate tissue at the same time. This advantage makes it the ideal surgical tool for the gastroenterologist.

Electrosurgical Generators provide the high frequency electrical energy required to perform electrosurgery and some of these are equipped with an option to use argon gas enhanced electrosurgery. Argon gas enhanced or Argon Plasma Coagulation (APC) has been in long use in the operating room setting and is used intermittently, usually for parenchymal organ surgeries.

Argon plasma equipped electrosurgery systems were adapted to be able to be used in flexible endoscopic procedures of the gut and lung.

Optical emission spectroscopy is known in the art and is commonly used to identify chemical composition and abundance of chemical species in mixtures. Plasma may excite the mixture, and the emitted fluorescence is collected and analyzed in a spectrometer.

Large amount of research was devoted to laser tissue welding. Companies such as Laser Tissue Welding Inc. (Texas, USA) have started clinical trials in 2009. This company targets for internal organs closure. Seraffix, an Israeli startup company using a robotic CO2 laser device also started clinical trials in 2009. Laser soldering utilizes IR laser (wavelength>1 um), mostly CO2 source, which activates thermally albumin that is applied pre activation. The laser grater advantage is its spatial accuracy which can get to micrometers resolution. However, for soldering application, the spatial accuracy is of less importance.

The main disadvantage of the laser is that its thermal activation is linearly dependent on the time it "hits" the targeted area; this means that if the laser beam stays too long on the same spot, it burns the albumin and the tissue in vicinity, performs poor adhesion and tissue necrosis.

U.S. Pat. No. 7,033,348; titled "Gelatin based on Powergel™ as solders for Cr4+ laser tissue welding and sealing of lung air leak and fistulas in organs"; to Alfano, R. et. al; discloses a method of welding tissue, involves joining edges of tissue wound and irradiating wound with laser selected from group consisting of Cr4+ lasers, semiconductor lasers and fiber lasers where the weld strength follows the absorption spectrum of water. The use of gelatin and esterified gelatin as solders in conjunction with laser inducted tissue welding impart much stronger tensile and torque strengths than albumin solders. Selected NIR wavelength from the above lasers can improve welding and avoid thermal injury to tissue when used alone or with gelatin and esterified gelatin solders. These discoveries can be used to enhance laser tissue welding of tissues such as skin, mucous, bone, blood vessel, nerve, brain, liver, pancreas, spleen, kidney, lung, bronchus, respiratory track, urinary tract, gastrointestinal tract, or gynecologic tract and as a sealant for pulmonary air leaks and fistulas such as intestinal, rectal and urinary fistulas.

US application 20060217706; titled "Tissue welding and cutting apparatus and method"; to Lau, Liming, et. al.; discloses a surgical apparatus and methods for severing and welding tissue, in particular blood vessels. The apparatus includes an elongated shaft having a pair of relatively movable jaws at a distal end thereof. A first heating element on one of the jaws is adapted to heat up to a first temperature and form a welded region within the tissue, while a second heating element on one of the jaws is adapted to heat up to a second temperature and sever the tissue within the welded region.

U.S. Pat. No. 7,112,201; titled "Electrosurgical instrument and method of use"; to Truckai, Csaba, et. al.; discloses an electrosurgical medical device and method for creating thermal welds in engaged tissue. In one embodiment, at least one jaw of the instrument defines a tissue engagement plane carrying a conductive-resistive matrix of a conductively-doped non-conductive elastomer. The engagement surface portions thus can be described as a positive temperature coefficient material that has a unique selected decreased electrical conductance at each selected increased temperature thereof over a targeted treatment range. The conductive-resistive matrix can be engineered to bracket a targeted thermal treatment range, for example about 60° C. to 80° C., at which tissue welding can be accomplished. In one mode of operation, the engagement plane will automatically modulate and spatially localize Ohmic heating within the engaged tissue from RF energy application-across micron-scale portions of the engagement surface. In another mode of operation, a conductive-resistive matrix can induce a "wave" of RF energy density to sweep across the tissue to thereby weld tissue.

US application 20030055417; titled "Surgical system for applying ultrasonic energy to tissue"; discloses an ultrasonic surgical instrument for sealing and welding blood tissues, having wave guide moving relative to introducer and ultrasound source coupled to elongated jaws moving to selected approximate position.

U.S. Pat. No. 6,323,037; titled "Composition for tissue welding and method of use"; to Lauto, Antonio, and Poppas, Dix P.; discloses a composition for tissue welding. The composition comprises an active compound, a solvent, and an energy converter and is insoluble in physiological fluids. A method for welding a tissue is also provided. The method comprises contacting a tissue with the above composition and exciting the composition such that the tissue becomes welded.

U.S. Pat. No. 7,186,659 titled "Plasma etching method"; to Fujimoto, Kotaro and Shimada, Takeshi; discloses an etching method for etching semiconductor devices, involves introducing etching gas in etching chamber, and exciting etching gas to plasma state to etch the material.

U.S. Pat. No. 6,197,026; titled "Electrosurgical instrument"; to Farin, Gunter and Grund, Karl Ernst; discloses an electrosurgical instrument for plasma coagulation of biological tissue e.g. for treating blood clots, haemostasis, thermal devitalization or destruction of pathological tissue.

US application 20080119843; titled "Compact electrosurgery apparatuses"; to Morris, Marcia; discloses a compact electrosurgical apparatus for use in electrosurgery such as flexible endoscopy.

U.S. Pat. No. 6,890,332; titled "Electrical discharge devices and techniques for medical procedures"; to Truckai, Csaba and Shadduck; discloses a medical instrument coupled to a source for introducing a gas to controllably form and capture transient gas volumes in a microchannel structure at the working surface of the instrument that interfaces with a targeted tissue site. Each of the microchannel features of the working surface carries an electrode element coupled to the electrical source. The energy may be applied to the targeted site in either of two modes of operation, depending in part on voltage and repetition rate of energy delivery. In one mode of energy application, electrical potential is selected to cause an intense electrical arc across the transient ionized gas volumes to cause an energy-tissue interaction characterized by tissue vaporization. In another preferred mode of energy delivery, the system applies selected levels of energy to the targeted site by means of energetic plasma at the instrument working surface to cause molecular volatilization of surface macromolecules thus resulting in material removal. Both modes of operation limit collateral thermal damage to tissue volumes adjacent to the targeted site.

U.S. Pat. No. 5,083,004; titled "Spectroscopic plasma torch for microwave induced plasmas"; to Wells, Gregory and Bolton, Barbara; discloses spectroscopic plasma torch suitable for use at atmospheric pressure.

SUMMARY OF THE INVENTION

The present invention relates to an apparatus and method for tissue welding applications using a plasma head.

In the context of the present application, the term "tissue welding" refers to procedures that cause otherwise separated tissue to be sealed, coagulated, fused, welded or otherwise joined together.

Process Control System:

Plasma welding process is preferably controlled such that the denaturization occurs to a satisfactory extent without harming the surrounding tissue. Thus, the local temperature should not exceed a predefined value (for example ~70° C.) and the duration of process in one location may be limited to the optimal activation duration.

Spectroscopy of the denaturization by the plasma is performed and evaluated as a process control method. Alternatively, an IR temperature measurement will be used.

Controller:

A control unit may receive readings from one or few of: RF signal measurement (transmitted and optionally reflected power), and gas flow controller and temperature sensors. The controller processes the inputs it received, and adjusts the RF signal power and gas flow accordingly.

The controller may be a standard STD OEM part or a dedicated electronics.

The albumin activation by the plasma process is based on thermal conduction and electric energy. The above suggests that the process maximum temperature is limited to the plasma temperature that is—if the plasma temperature is maintained near or below 70° C. or less, the temperature diffused to the processed area can't exceed 70° C. The temperature control of the plasma is very accurate and can be adjusted easily as needed for the specific application. However, the plasma temperature can be raised to very high values by increasing RF power/frequency and reducing gas flow rates. Such conditions may be used for ablation or coagulation of tissue.

An advantage for using plasma for tissue welding is the antiseptic properties of the plasma.

The plasma discharge emits light in the entire wavelength spectrum range. The Albumin can be engineered in a way that its activation will be enhanced by the plasma light. Moreover, the light emitted by the plasma can be analyzed by the standard known spectroscopy methods for process control use.

Kind of Plasma:

The plasma can be adjusted in various ways to have different characteristics:

"Arcing plasma", were the patient body serves as the ground electrode for example (mono-polar configuration), induces a direct RF power on the processed surface and performs a superficial activation. In arcing plasma, the high potential "breaks" and ablates the tissue.

"Non-arcing" plasma, performs a thermal activation more than electrical (electric potential still exist but in less extent).

The proposed device and method overcome the existing drawbacks and may: Decrease in morbidity and mortality; Reduce external infections; Allows reduction of voids in the tissue which may become infections/abscess; Decrease operating time; Enable control of bleeding; Provide plasma coagulation; Shorten hospital stay; Decreases healthcare costs; and Conserve of blood products by reducing transfusion requirements.

In some embodiments, plasma parameters are adjusted according to the desired effect on the tissue and/or the gluing material such as albumin solution added.

For example, and without limitation, superficial effect may be achieve using high ion bombardment applied by applying plasma at positive voltage in comparison to the grounded tissue (so called DC-Bias, as used in semi conductors industry). High "plasma temperature", wherein the plasma gas itself gets to high temperature may be used for short duration for cleaning and disinfecting the tissue surface before and/or after the welding causing a superficial effect enabling superficial charring of surface without deep thermal effect.

For example, and without limitation, plasma parameters may be low gas flow (0.1-2 Liter/Minute), high voltage, lower frequency (500 KHz-2 MHz), pulsed plasma (250 ms on, 500 ms off), using Argon as bombarding gas, and CCP excitation configuration (Capacitive Coupled Plasma—direct contact between electrode to gas).

It is an aspect of the current invention to provide a medical method of tissue welding comprising: applying to the tissue to be welded, bio-compatible liquid capable of solidifying in response to application of plasma; and applying plasma to said bio-compatible liquid, wherein temperature of said plasma is less than 70 degrees Celsius. The medical method of claim 1 wherein said bio-compatible liquid is albumin solution.

In some embodiments the concentration of albumin in said bio-compatible liquid is at least 40%.

In some embodiments the plasma comprises He gas.

In some embodiments the plasma comprises substantially He gas.

In some embodiments the plasma comprises gases such as argon; helium; oxygen and SF6.

In some embodiments the plasma comprises ionization gas and chemically reactive gas, wherein said chemically reactive gas is capable of forming chemical reaction with said bio-compatible liquid, wherein said reaction assists in solidifying said bio-compatible liquid.

In some embodiments the chemically reactive gas is a polymerizing gas.

In some embodiments the chemically reactive gas comprises substances such as: CHF3 or CH3F.

In some embodiments the temperature of said plasma is maintained using feedback mechanism.

In some embodiments the feedback mechanism comprises measuring RF power.

In some embodiments the feedback mechanism comprises measuring RF impedance.

In some embodiments the feedback mechanism comprises measuring optical spectra emitted from the plasma.

In some embodiments the plasma is excited by a bi-polar electrode configuration.

In some embodiments the plasma is excited by a mono-polar electrode configuration.

In some embodiments the plasma is excited by an electrode configuration combining bi-polar and mono-polar electrodes.

In some embodiments the plasma is excited by inductive coil.

It is another aspect of the current invention to provide a hand held medical device for tissue welding comprising: a body capable to be held and manipulated by a single human hand, said body comprising: a battery providing electrical power; gas handling sub-system comprising: a gas tank storing plasma gas under high pressure; gas pressure reduction and flow control mechanism; RF circuit comprising: RF generator; RF amplifier; and RF impedance matching circuitry; and a tip comprising: a plasma tube having a proximal opening and a distal opening, receiving gas from said gas handling sub-system through its proximal opening and providing plasma through its distal opening; and plasma exciter, exciting said gas in said plasma tube to plasma.

In some embodiments the hand held medical device further comprising a bio-compatible liquid injector comprising: a bio-compatible liquid reservoir; liquid transport subsystem, transporting said bio-compatible liquid from said reservoir to a nozzle; and a liquid nozzle, located in proximity to said distal opening of said plasma tube, wherein said bio-compatible liquid capable of solidifying in response to application of plasma.

In some embodiments the tip is capable to detach from said body of said hand held medical device.

In some embodiments the detachable tip is one use disposable tip.

In some embodiments the detachable tip can be replaced with an ablation tip comprising an elongated mono-polar plasma electrode.

In some embodiments the plasma exciter comprises bi-polar electrodes.

In some embodiments the held medical device further comprising a grounding electrode, electrically grounding the tissue to be welded in respect to said RF circuit.

In some embodiments the plasma exciter comprises an induction coil.

In some embodiments the temperature of said plasma is less than 70 degrees Celsius.

In some embodiments the bio-compatible liquid is albumin solution.

In some embodiments the distal opening of said tube is aimed in a direction substantially different than the long axis of said plasma tube.

It is yet another aspect of the current invention to provide a compact medical device for tissue welding comprising: a supply and control unit comprising: a battery providing electrical power; gas handling sub-system comprising: a gas tank storing plasma gas under high pressure; gas pressure reduction and flow control mechanism; RF circuit comprising: RF generator; RF amplifier; and RF impedance matching circuitry; a hose, transferring gas from said gas handling sub-system and RF signal from said RF circuit to a hand-held plasma head; and a plasma head capable to be held and manipulated by a single human hand, said plasma head comprising: a tip comprising: a body configured to be held by hand; a tip comprising: a plasma tube having a proximal opening and a distal opening, receiving gas through its proximal opening and providing plasma through its distal opening; and plasma exciter, exciting said gas in said plasma tube to plasma.

In some embodiments the compact medical device further comprising a bio-compatible liquid injector comprising: a bio-compatible liquid reservoir; liquid transport subsystem, transporting said bio-compatible liquid from said reservoir to a nozzle; and a liquid nozzle, located in proximity to said distal opening of said plasma tube, wherein said bio-compatible liquid capable of solidifying in response to application of plasma.

In some embodiments the said tip is capable to detach from said body of said hand held medical device.

In some embodiments the detachable tip is one use disposable tip.

The compact medical device of claim 30 wherein said detachable tip can be replaced with an ablation tip comprising an elongated mono-polar plasma electrode.

In some embodiments the plasma exciter comprises bi-polar electrodes.

In some embodiments the compact medical device further comprising a grounding electrode, electrically grounding the tissue to be welded in respect to said RF circuit.

In some embodiments the plasma exciter comprises an induction coil.

In some embodiments the temperature of said plasma is less than 70 degrees Celsius.

In some embodiments the said bio-compatible liquid is albumin solution.

In some embodiments the said distal opening of said tube is aimed in a direction substantially different than the long axis of said plasma tube.

In some embodiments the plasma head further comprises at least one control input for controlling the operation of said supply and control unit.

In some embodiments the supply and control unit further comprises a controller, said controller capable of receiving user input and plasma feedback signal and to adjust operation of at least one of: gas handling sub-system and RF circuit in response to said user input and plasma feedback signal.

In some embodiments the temperature of said plasma is maintained at less than 70 degrees Celsius using said feedback mechanism.

In some embodiments the generating said feedback signal comprises measuring RF power.

In some embodiments the generating said feedback signal comprises measuring RF impedance.

In some embodiments the aid supply and control unit further comprises a plasma spectroscope, and wherein generating said feedback signal comprises measuring emission spectra of said plasma.

In some embodiments the compact medical device further comprises an optical fiber collecting plasma emission radiation at its distal end which is located proximately to said plasma tube and transferring said radiation to said spectrometer.

In some embodiments the generating said feedback signal comprises measuring said tissue temperature using an IR sensor.

An isolating RF transformer may be used to float the RF signal in respect to the patient body or ground potential.

Additionally, a variable load may be used to control RF current.

Plasma heads configured for deep cuts and long cuts are provided.

For long cuts, a device with two plasma heads is disclosed. The two plasma heads are placed along the cut and coagulate an elongated stretch of cut at a time.

Alternatively, an elongated plasma head with gas funnel chamber and a perforated shower plate may be used to ignite plasma having a length which is larger than its width. External; internal; or coil electrodes may be used.

For welding deep cuts, a needle electrode may be placed inside the cut to direct plasma or current to the depth of the cut.

In some embodiments the compact medical device further comprising a thin electrode inserted into the cut to be welded and capable of directing electrical current deep into the welded tissue.

In some embodiments the compact medical device further comprises a second plasma head capable of producing plasma and working simultaneously with said first plasma tip, thus enabling treatment of longer stretch of tissue than possible using a single plasma tip.

In some embodiments the compact medical device having a second plasma head further comprising a thin electrode inserted into the cut to be welded and capable of directing electrical current deep into the welded tissue.

In some embodiments the distal plasma opening has an elongated shape for treating elongated cut in tissue.

In some embodiments the compact medical device further the elongated plasma opening has rectangular shape measuring approximately 6 to 7 mm by 20 to 80 mm.

In some embodiments the compact medical device further comprising a perforated plate within the gas flow capable of substantially uniformly spread the flow of plasma.

In some embodiments the plasma is excited buy a coil looped around said distal plasma opening.

In some embodiments the plasma exciter comprises a ring electrode external to said plasma tube.

In some embodiments the plasma exciter comprises a ring electrode external to said plasma tube and an electrode internal to said plasma tube.

In some embodiments the electrode internal to said plasma tube is covered with electrical insulation layer.

In some embodiments the electrode internal to said plasma tube has helical shape.

In some embodiments the body configured to be held by hand is ergonomically shaped and is at an angle to said plasma tip.

In some embodiments the plasma tip further comprises at least one stand-off for determining distance between plasma and treated tissue.

It is another aspect of the invention is to provide a method of tissue welding comprising: applying albumin solution to a cut in a tissue; and applying plasma for solidifying said albumin solution, wherein temperature of said plasma is less than 70° C.

In some embodiments the method further comprises whipping excess albumin solution from said tissue with a wiper comprising: a handle; and a flexible wiper blade.

In some embodiments the wiper blade further comprises an indentation.

In some embodiments the method further comprises disinfecting the welding bed by applying plasma prior to said applying albumin solution to the cut. In some embodiments the plasma applied before applying albumin is in a form of a short, high temperature pulse.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

The invention is capable of other embodiments or of being practiced or carried out in various ways. Also, it is to be understood that the phraseology and terminology employed herein is for the purpose of description and should not be regarded as limiting.

In discussion of the various figures described herein below, like numbers refer to like parts. The drawings are generally not to scale. For clarity, non-essential elements were omitted from some of the drawings. Some optional parts were drawn using dashed lines.

In the drawings:

Figure 1:
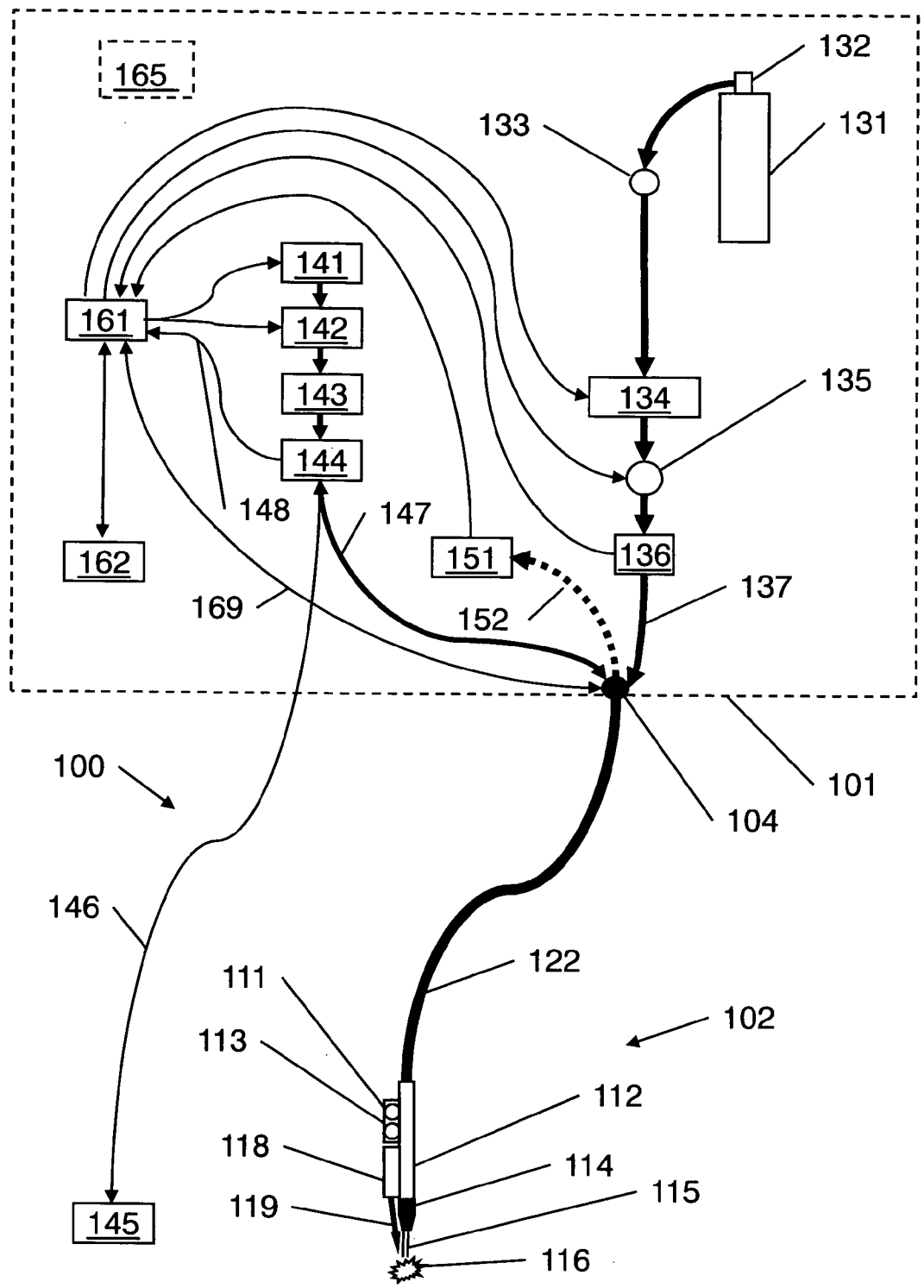
Figure 2:
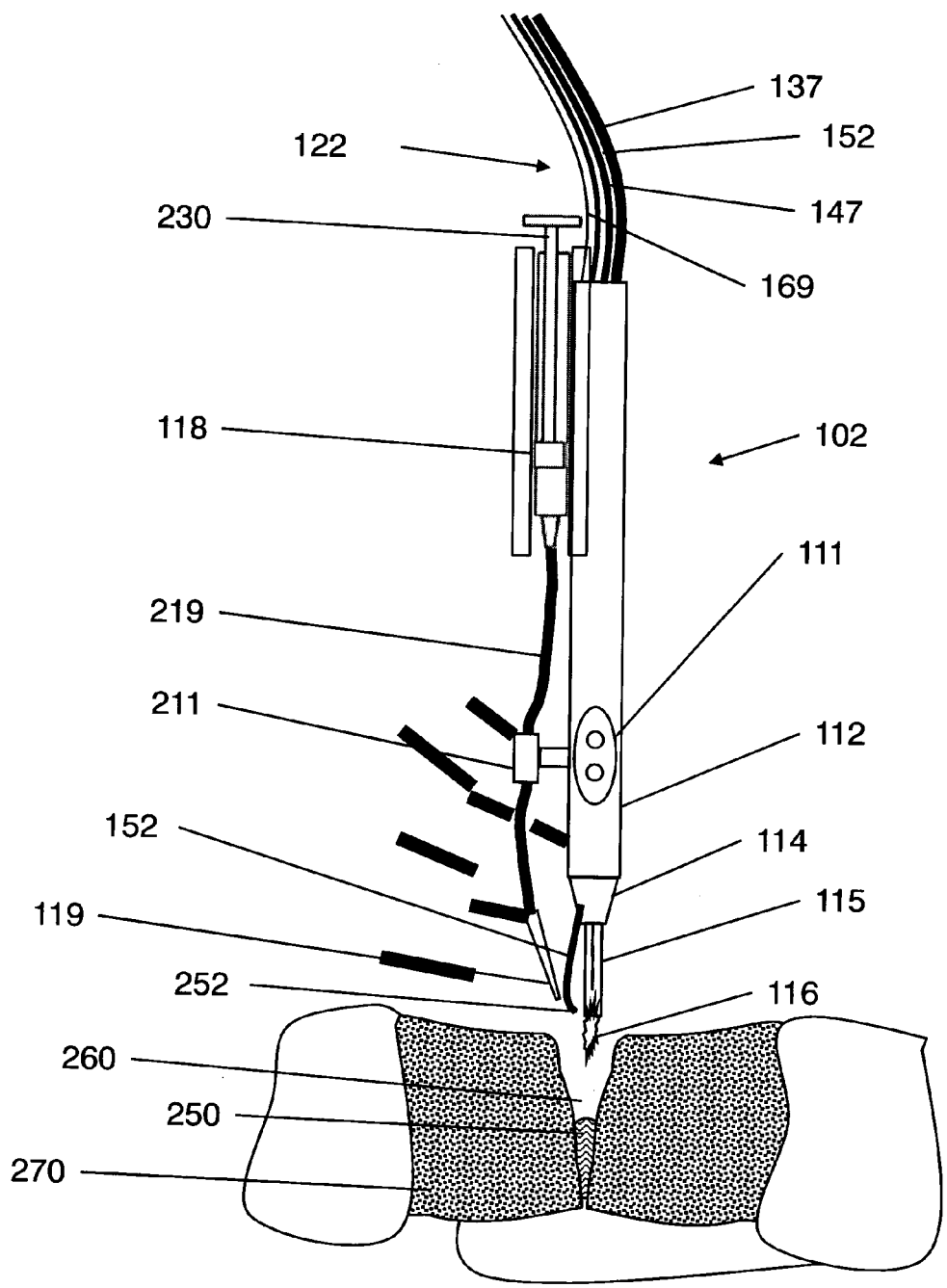

FIG. 1 schematically depicts a block diagram of plasma welding system according to an exemplary embodiment of the current invention;

FIG. 2 schematically depicts a hand held plasma head for plasma welding according to an exemplary embodiment of the current invention.

Figure 3A:
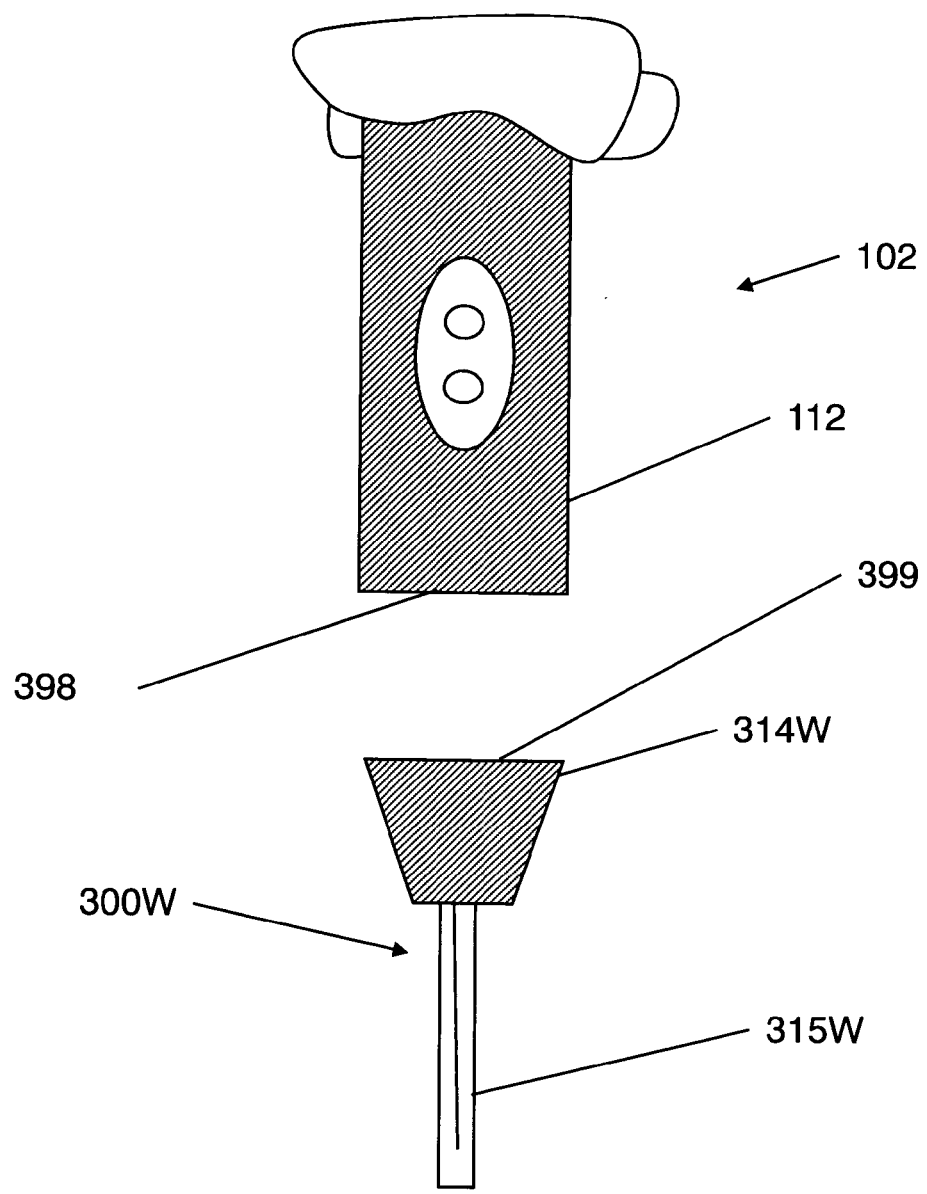
Figure 4A:
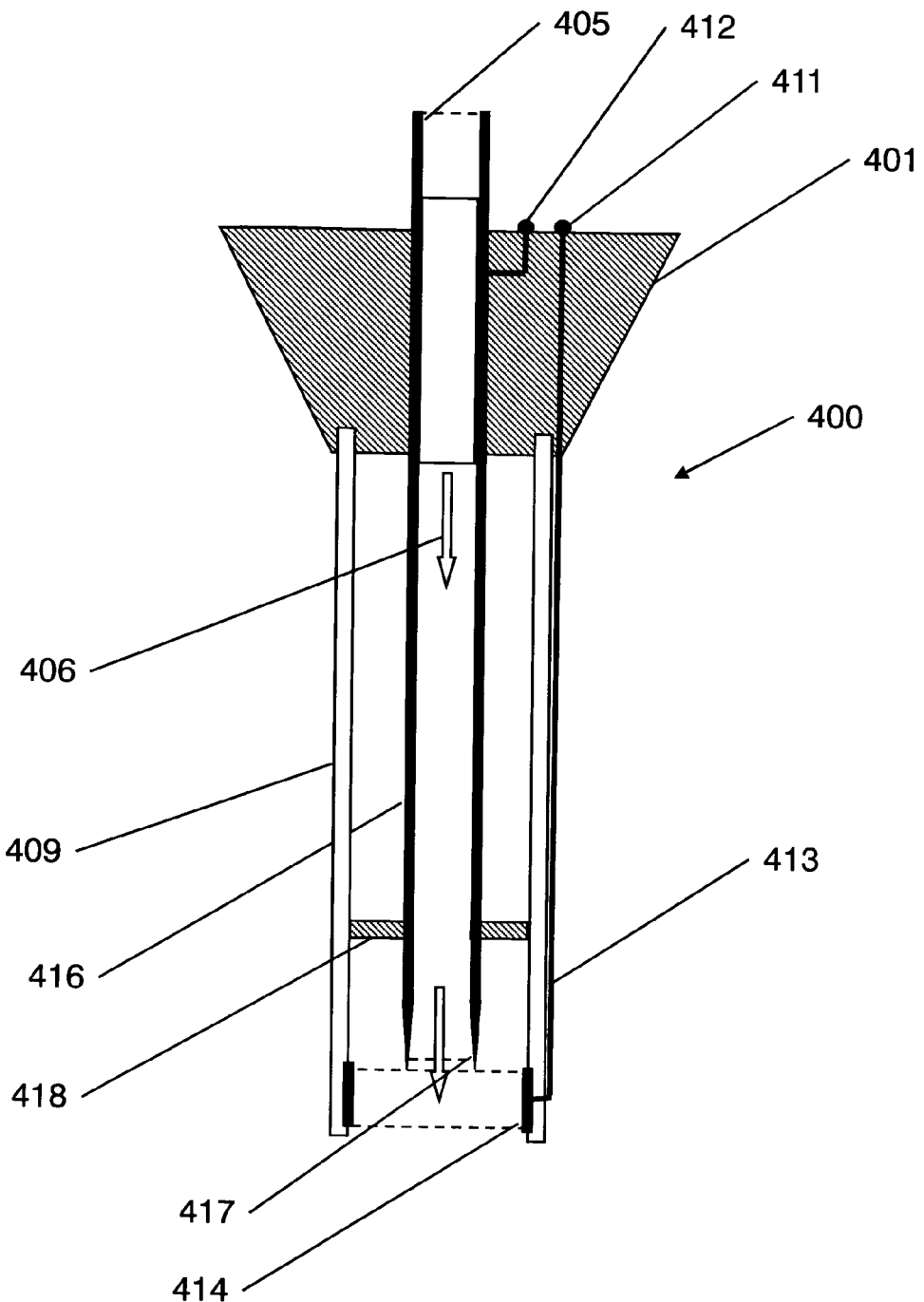
Figure 4C:
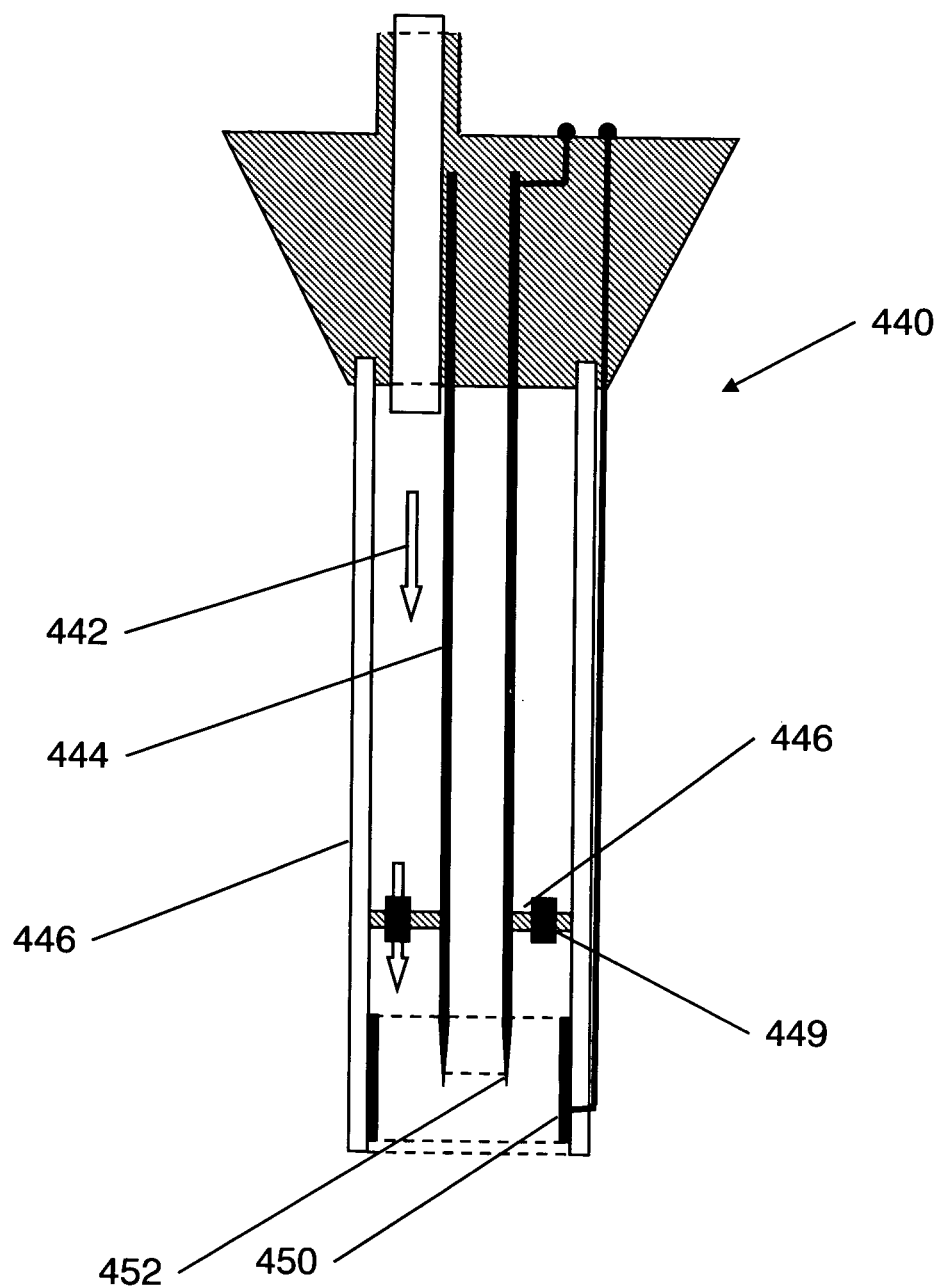
Figure 4D:
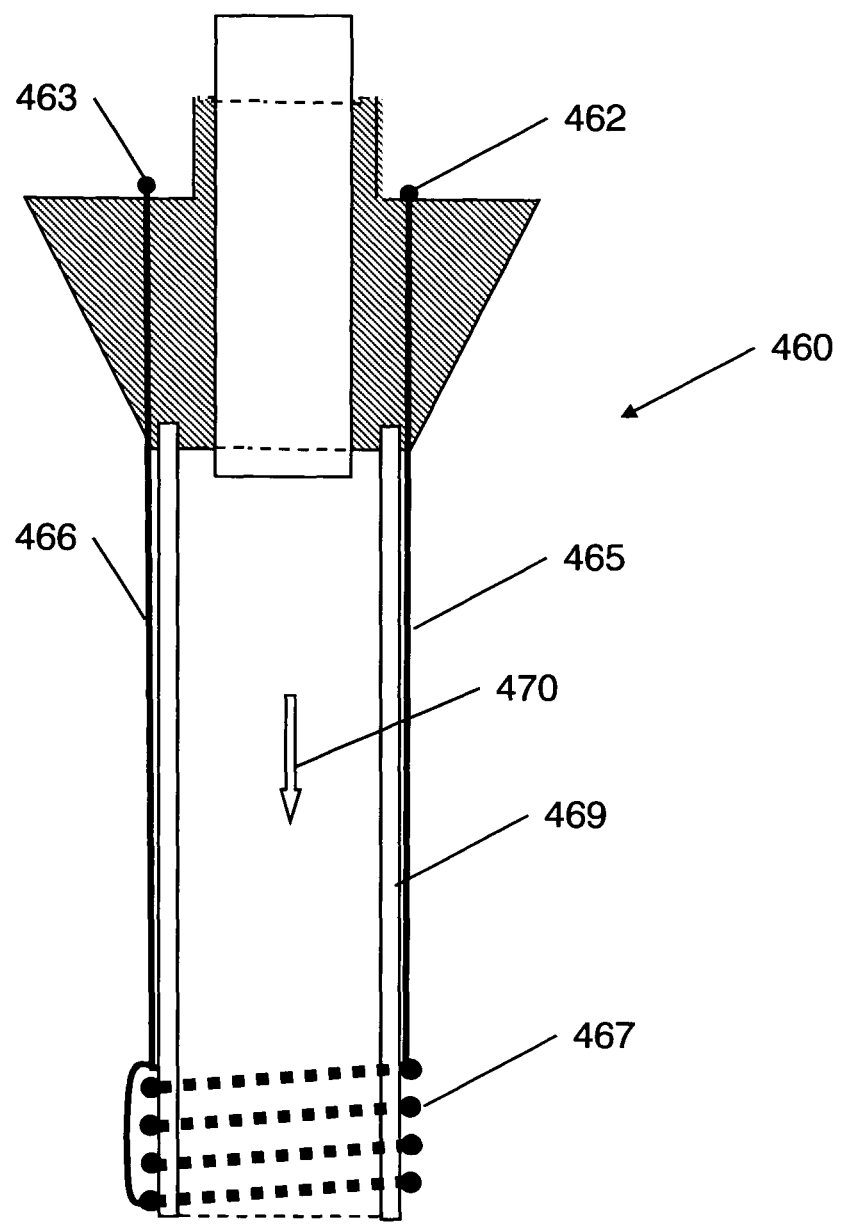
Figure 4F:
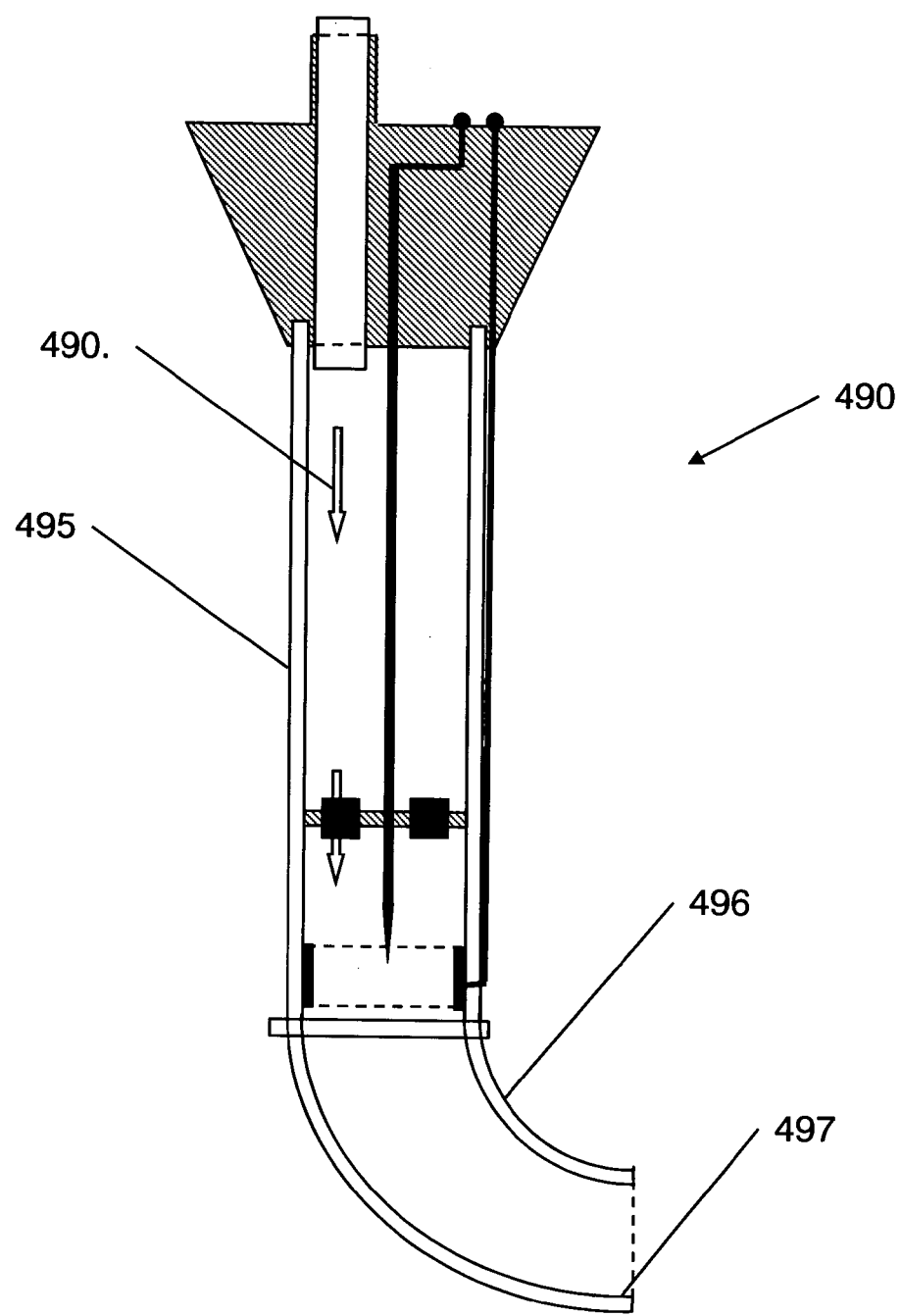
Figure 5A:
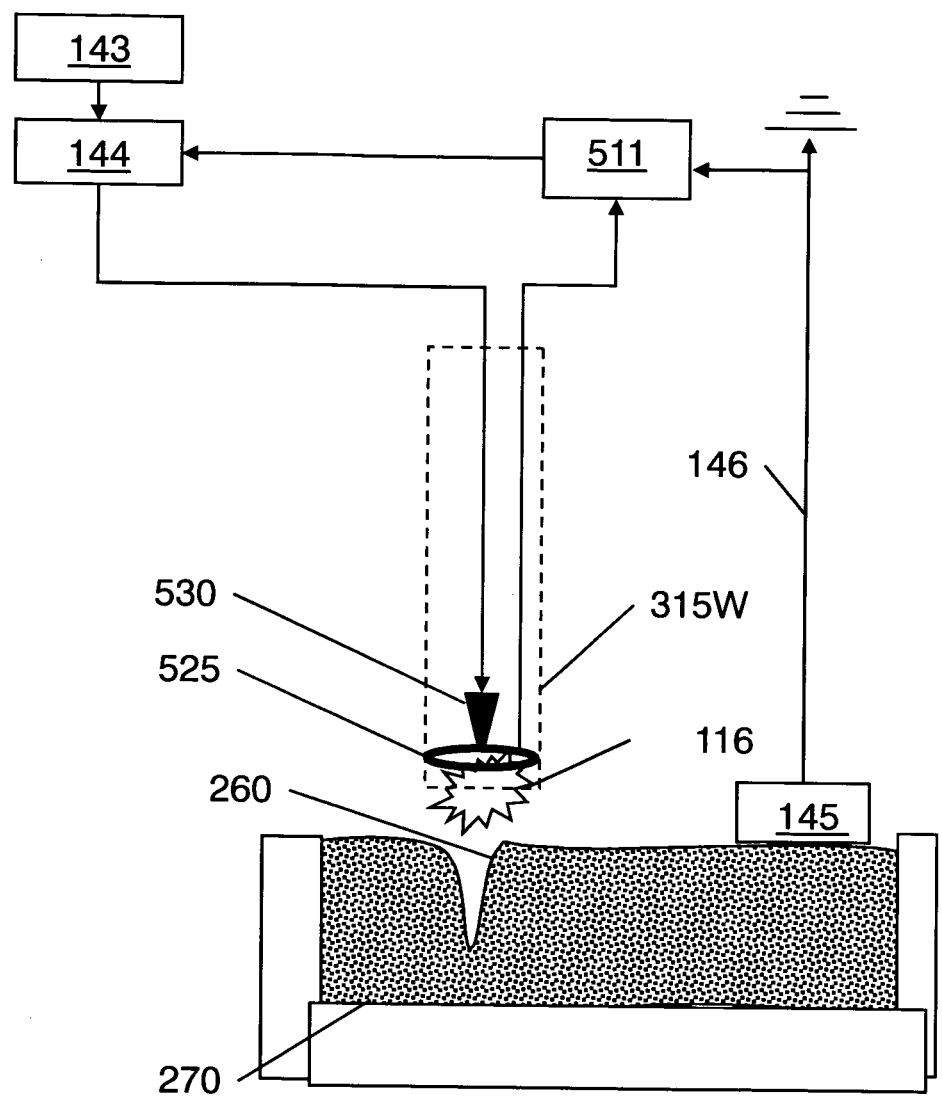
Figure 5B:
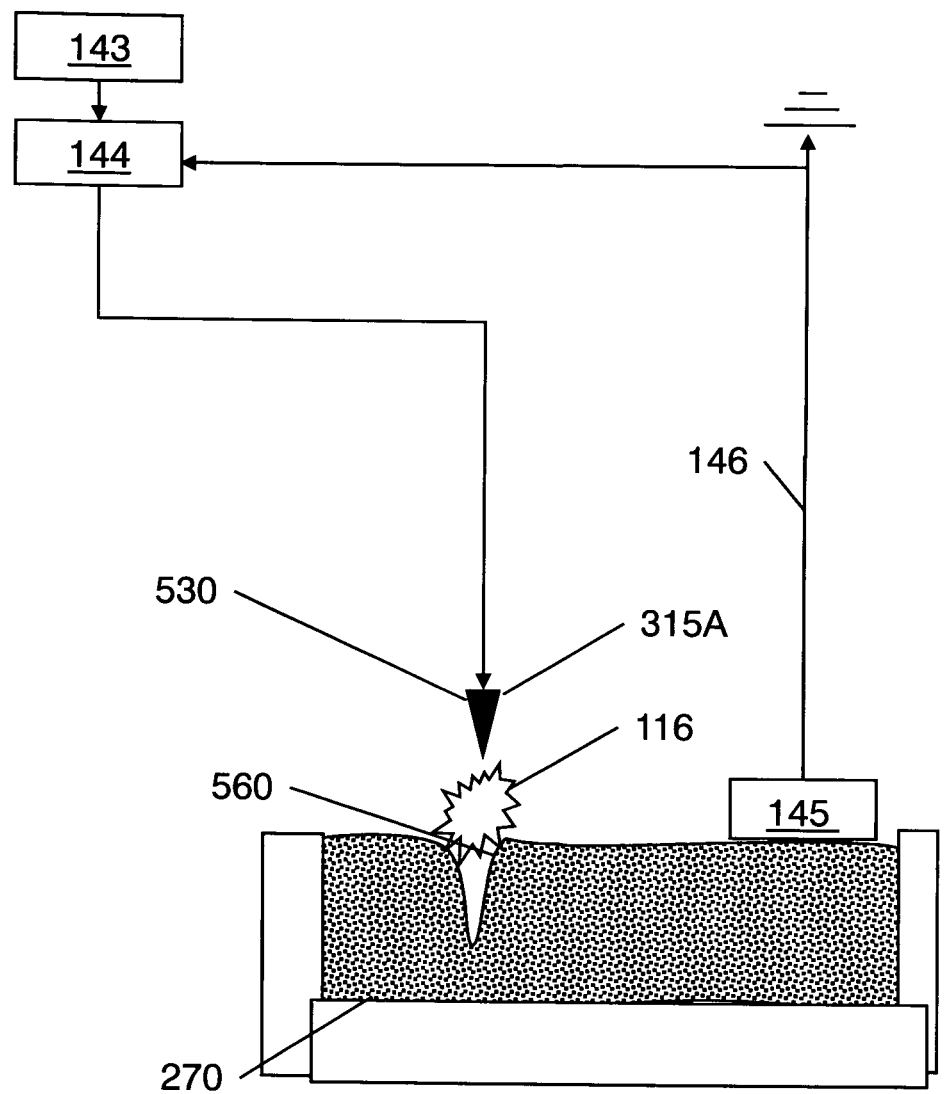
Figure 6:
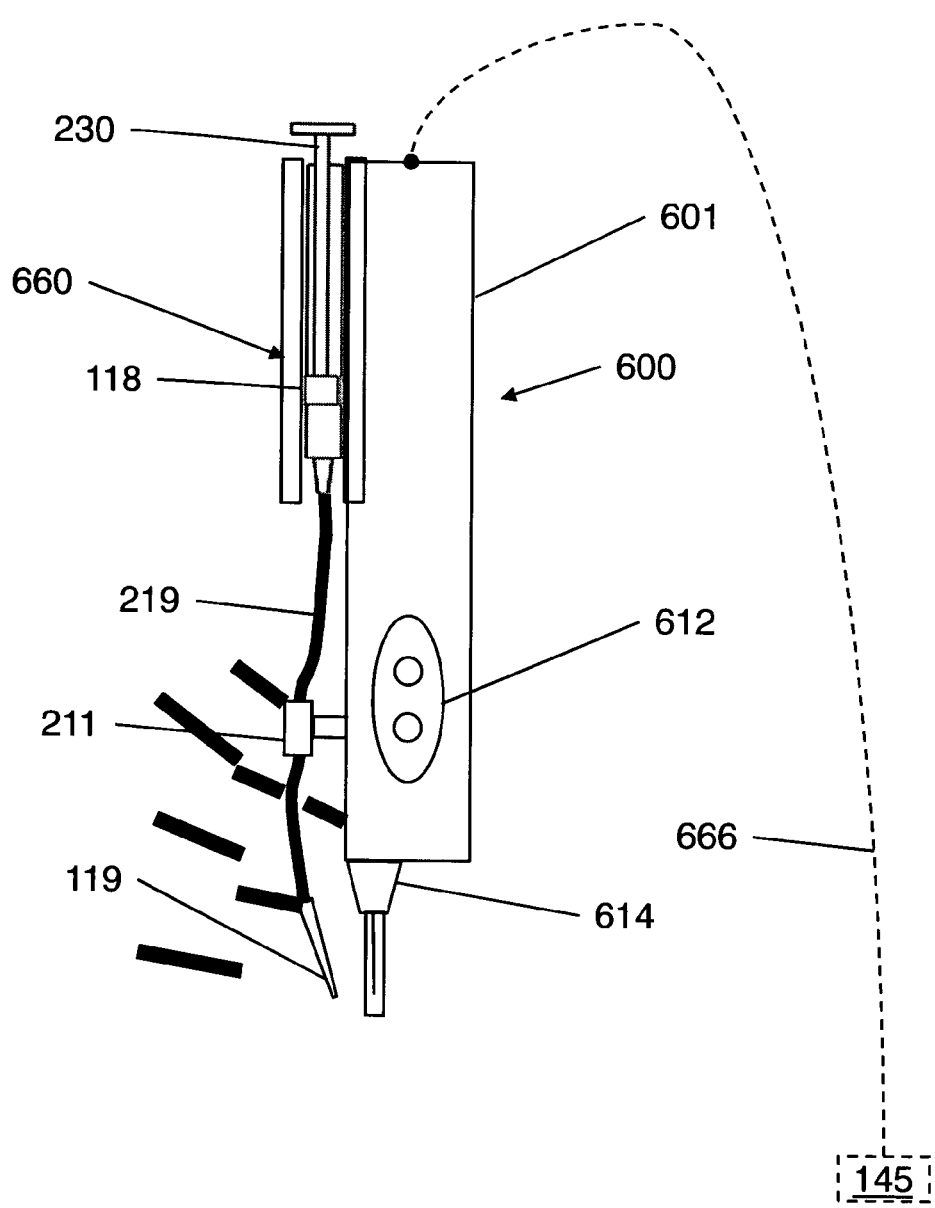
Figure 7A:
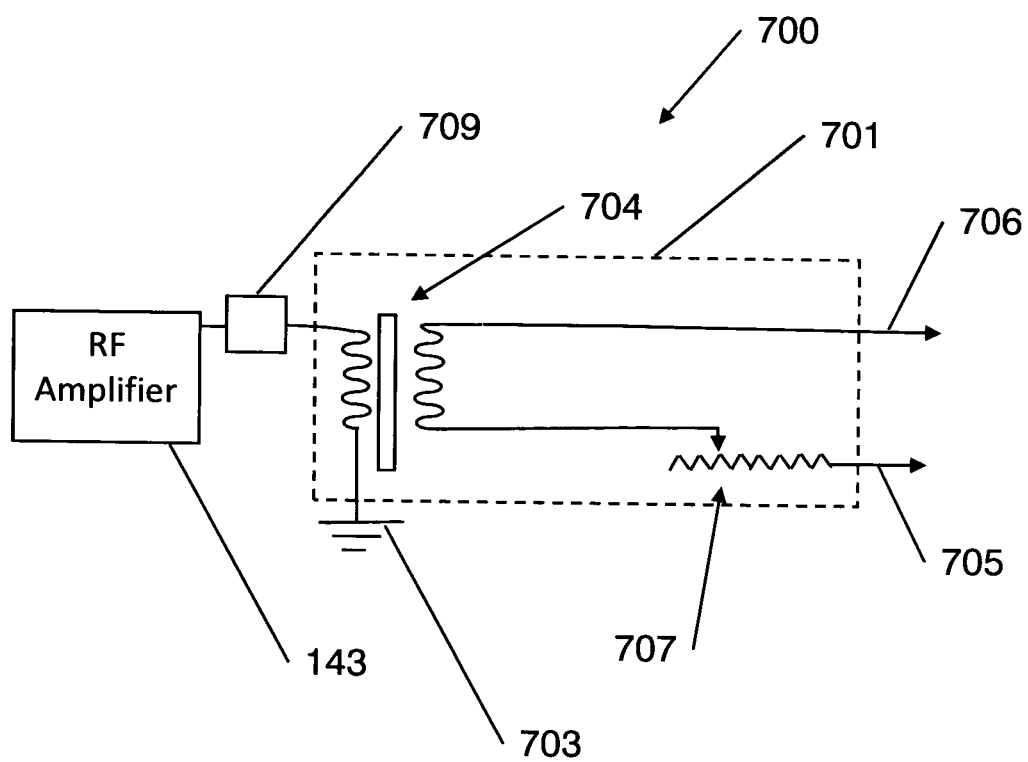
Figure 7B:
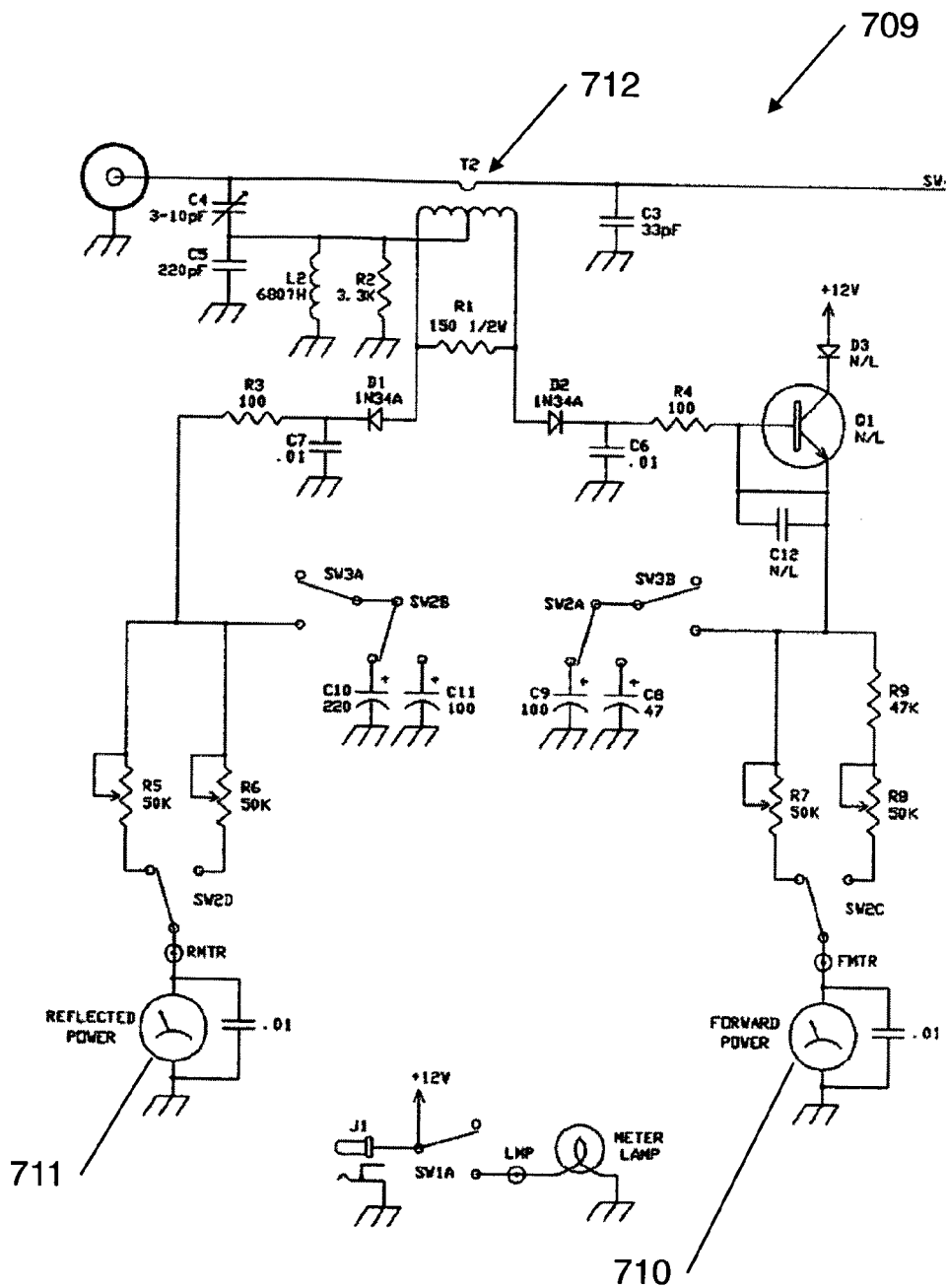
Figure 8A:
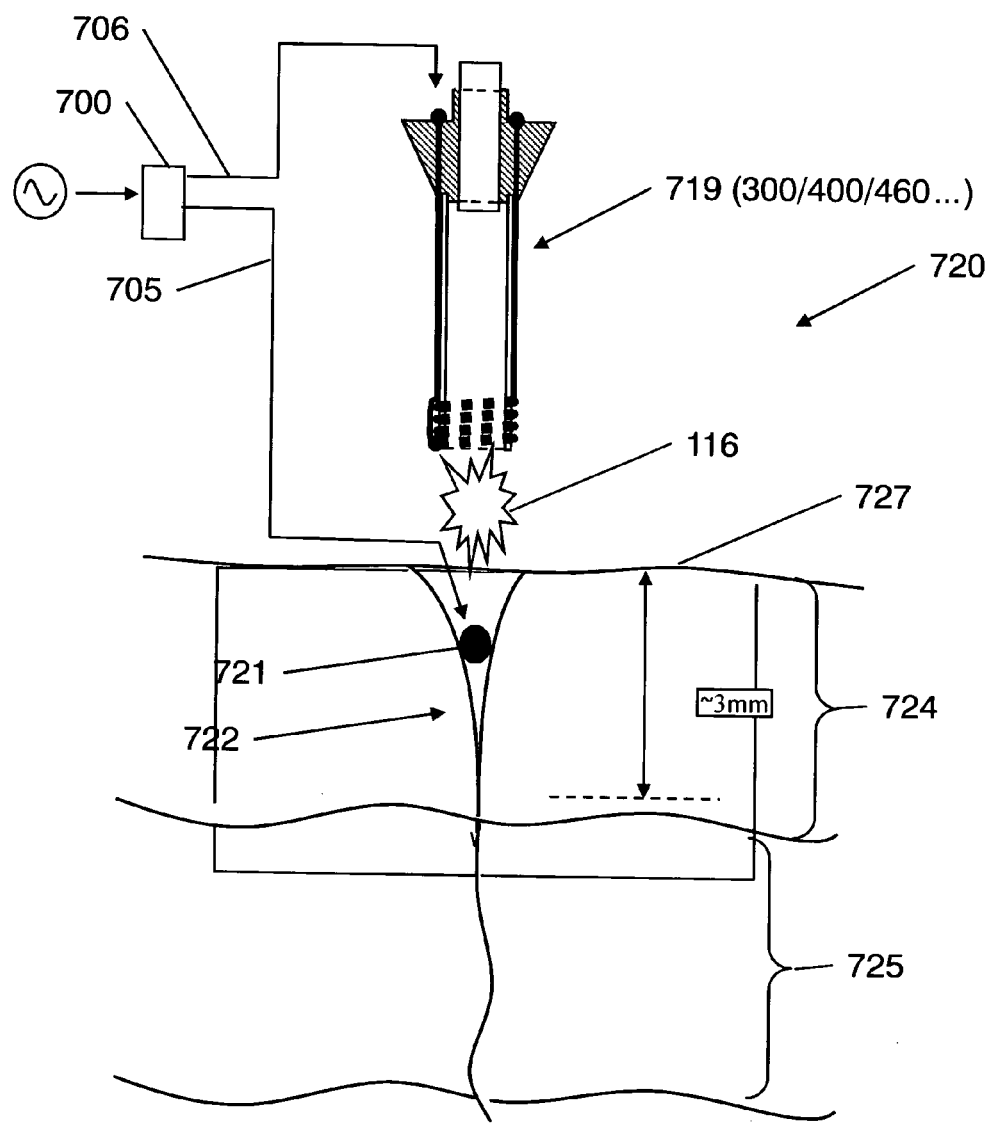
Figure 8B:
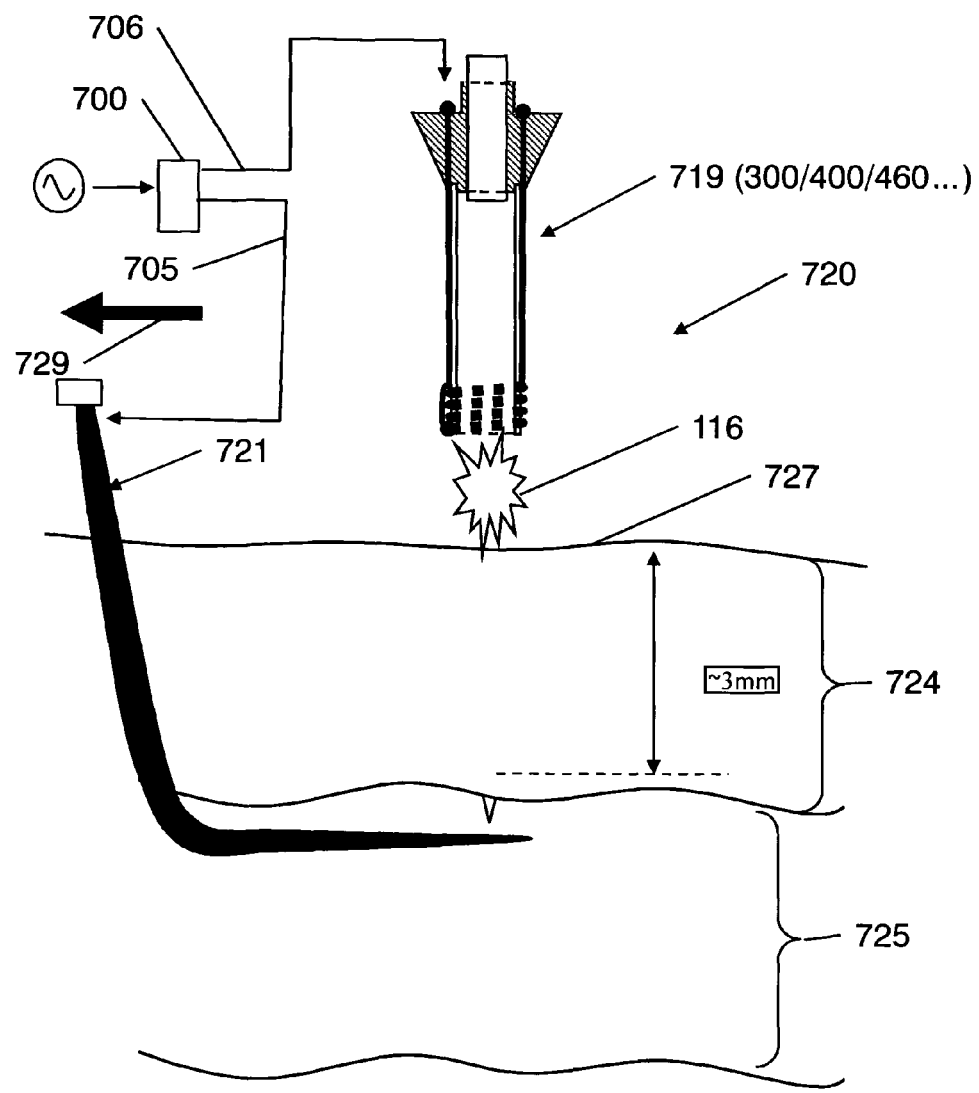
Figure 9A:
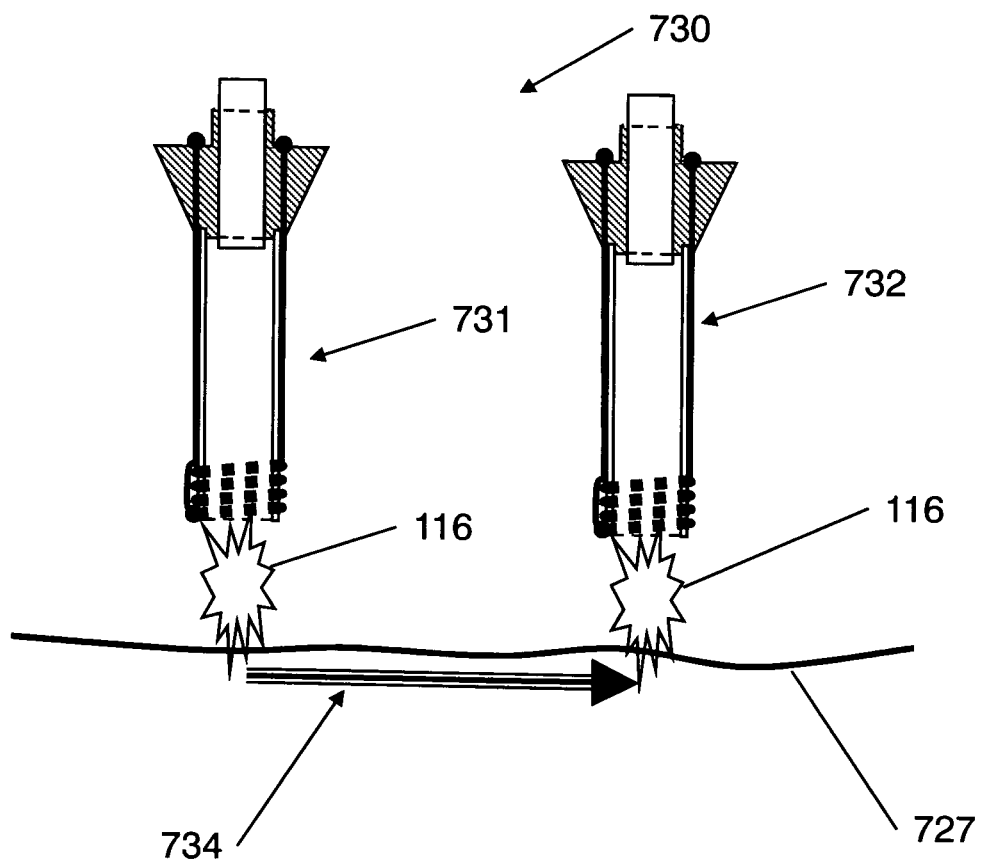
Figure 9B:
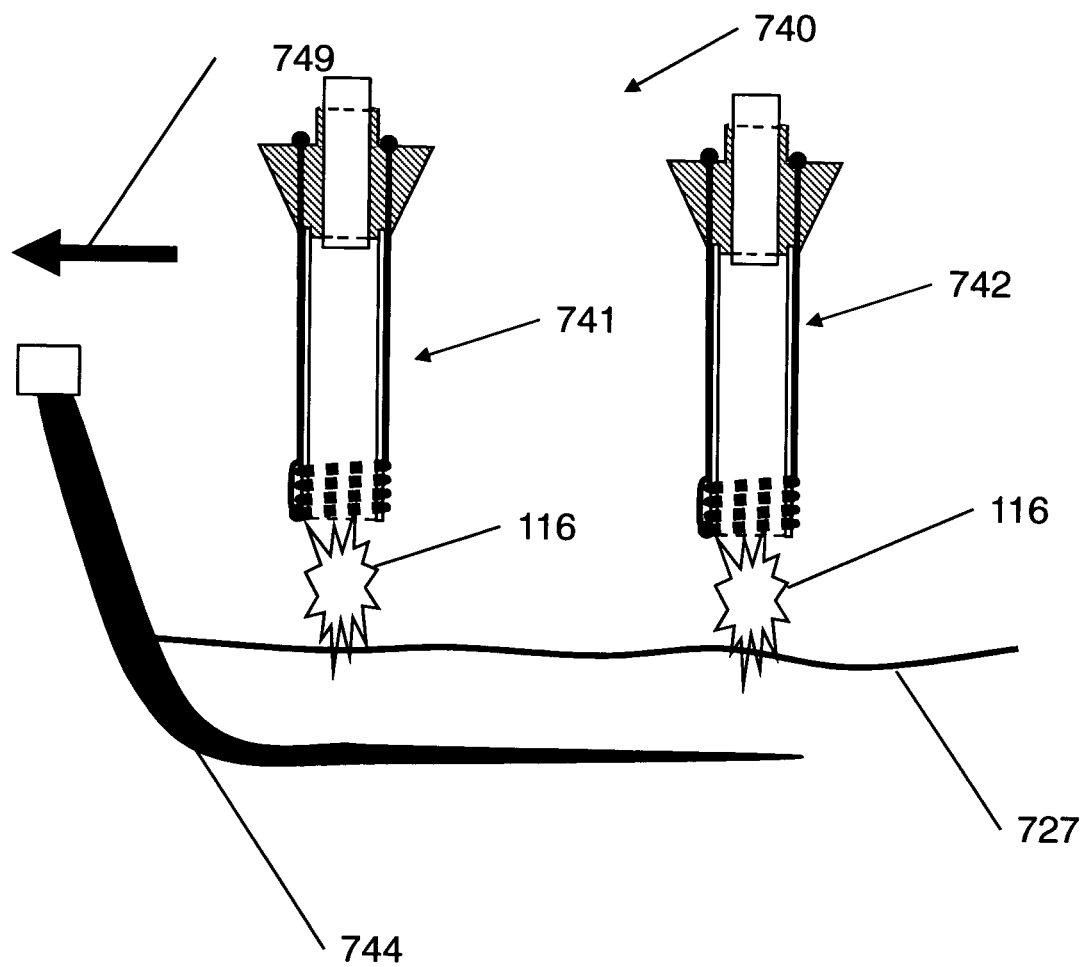
Figure 10A:
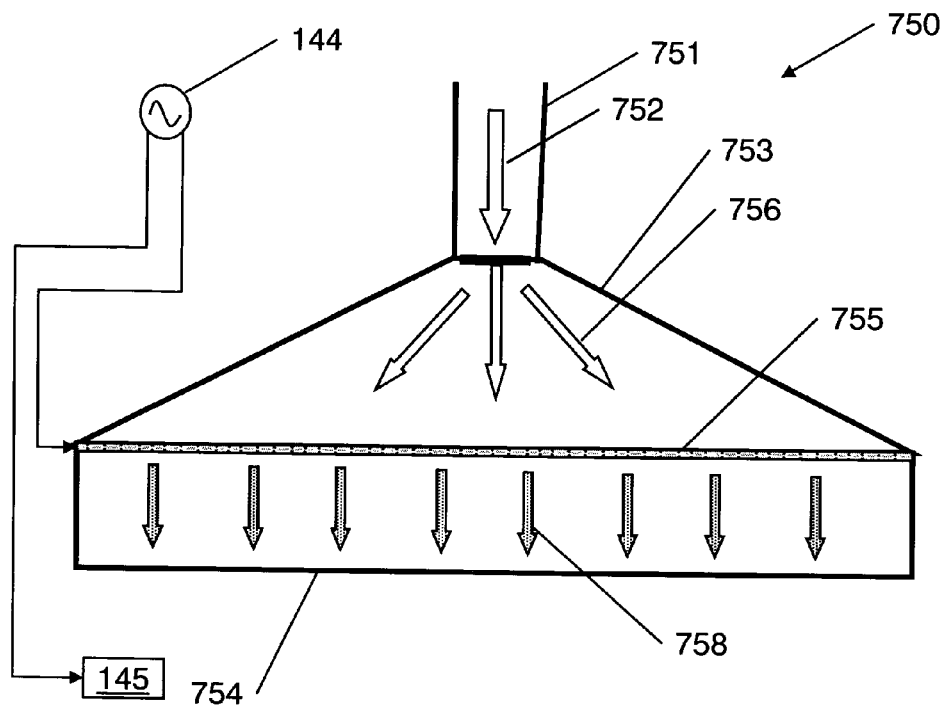
Figure 10B:
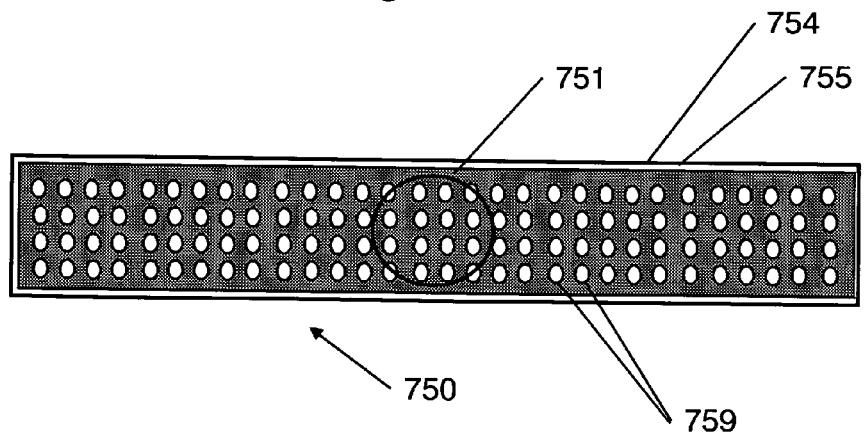
Figure 10C:
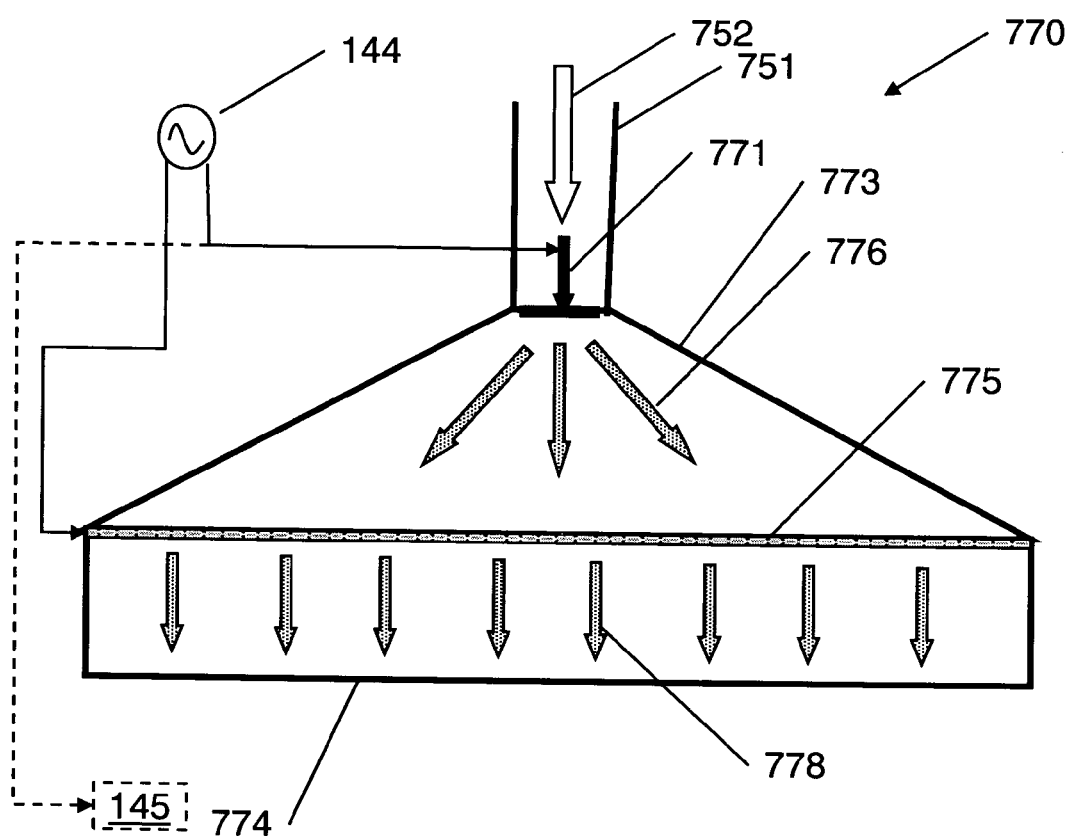
Figure 11:
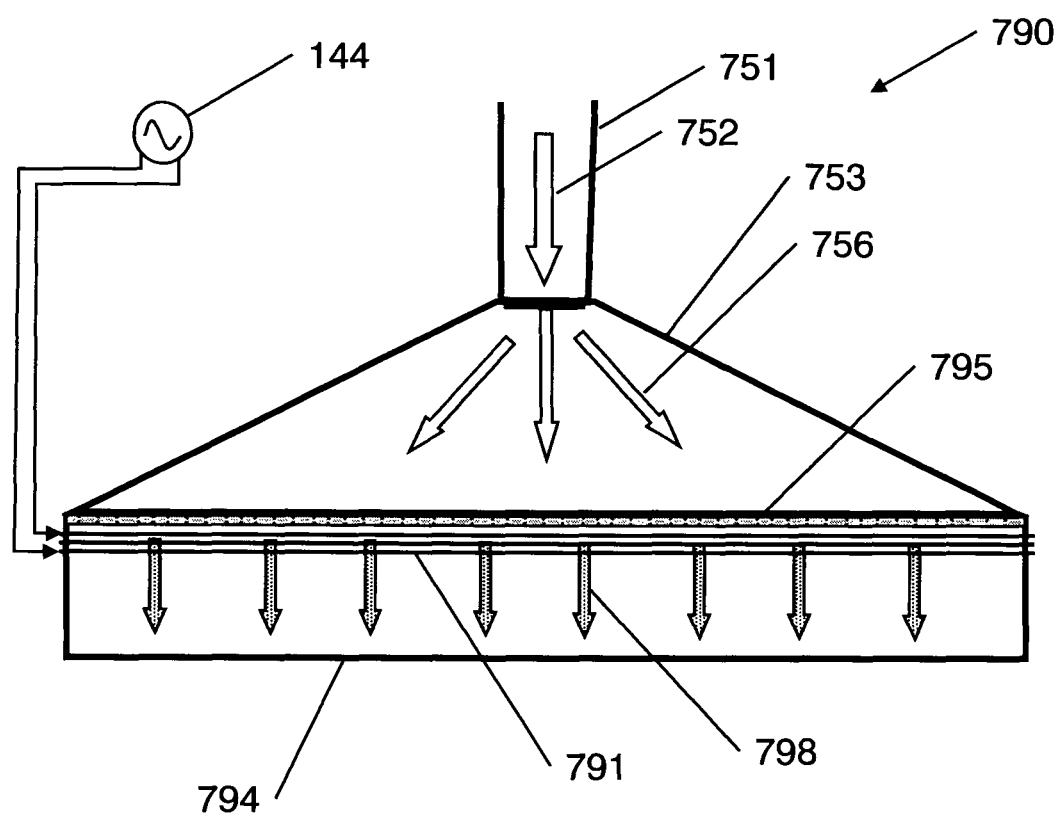
Figure 12:
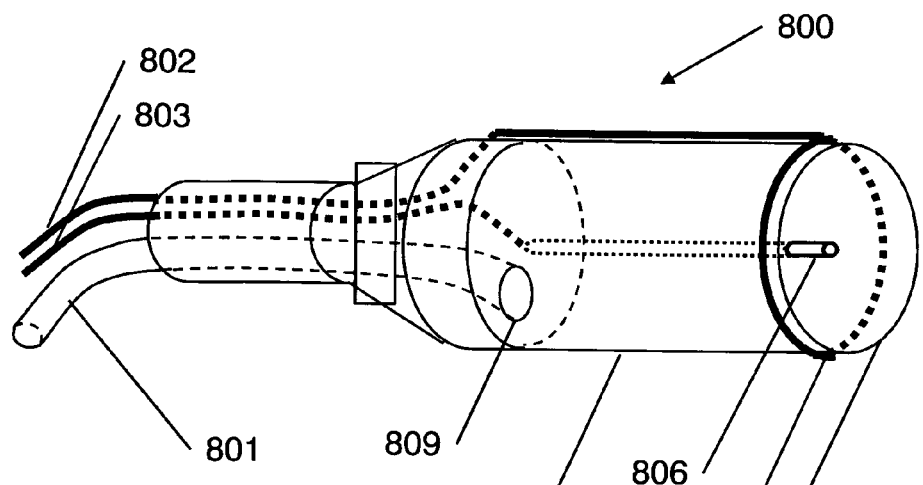
Figure 13:
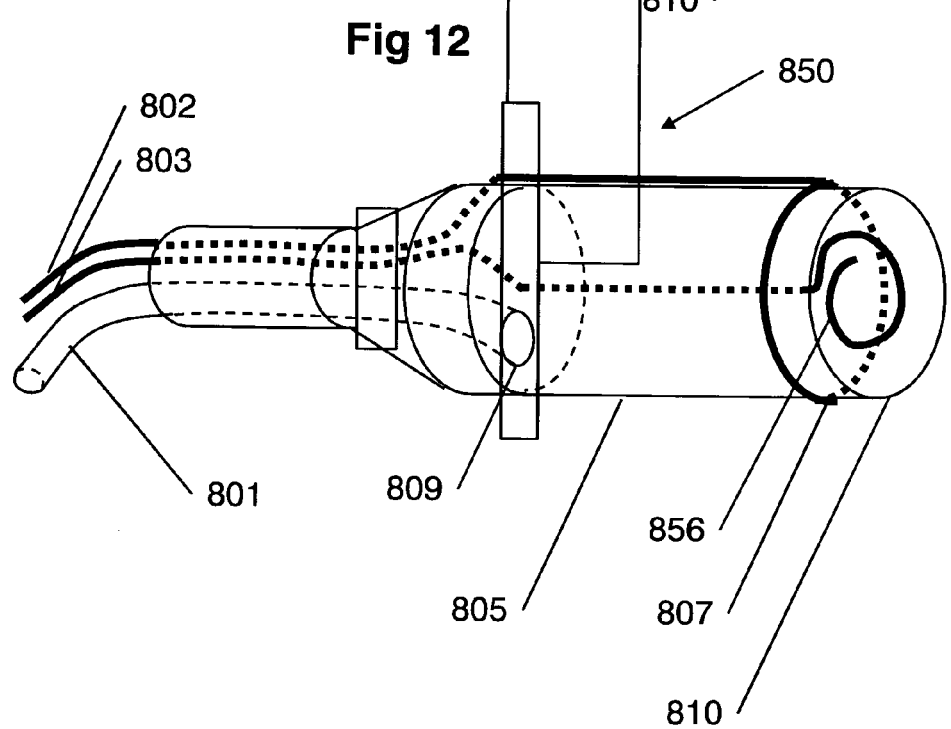
Figure 14:
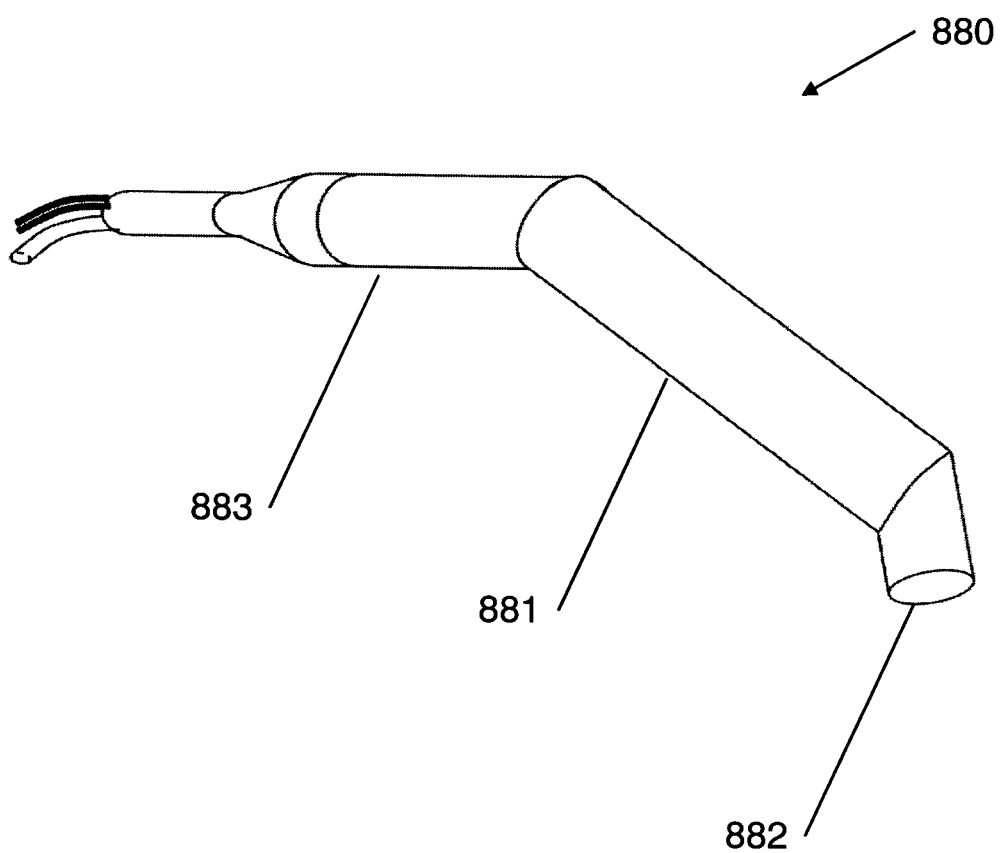
Figure 15:
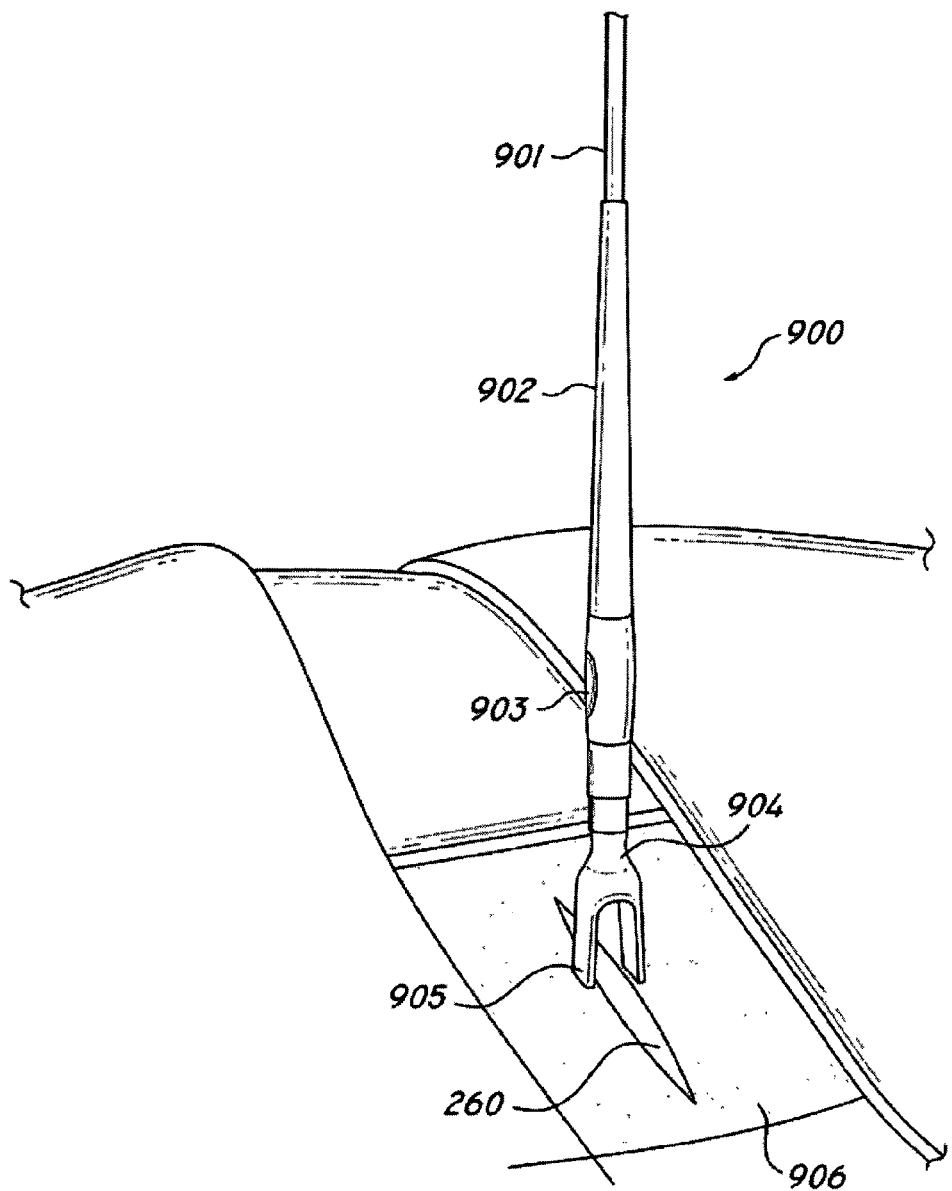
Figure 16:
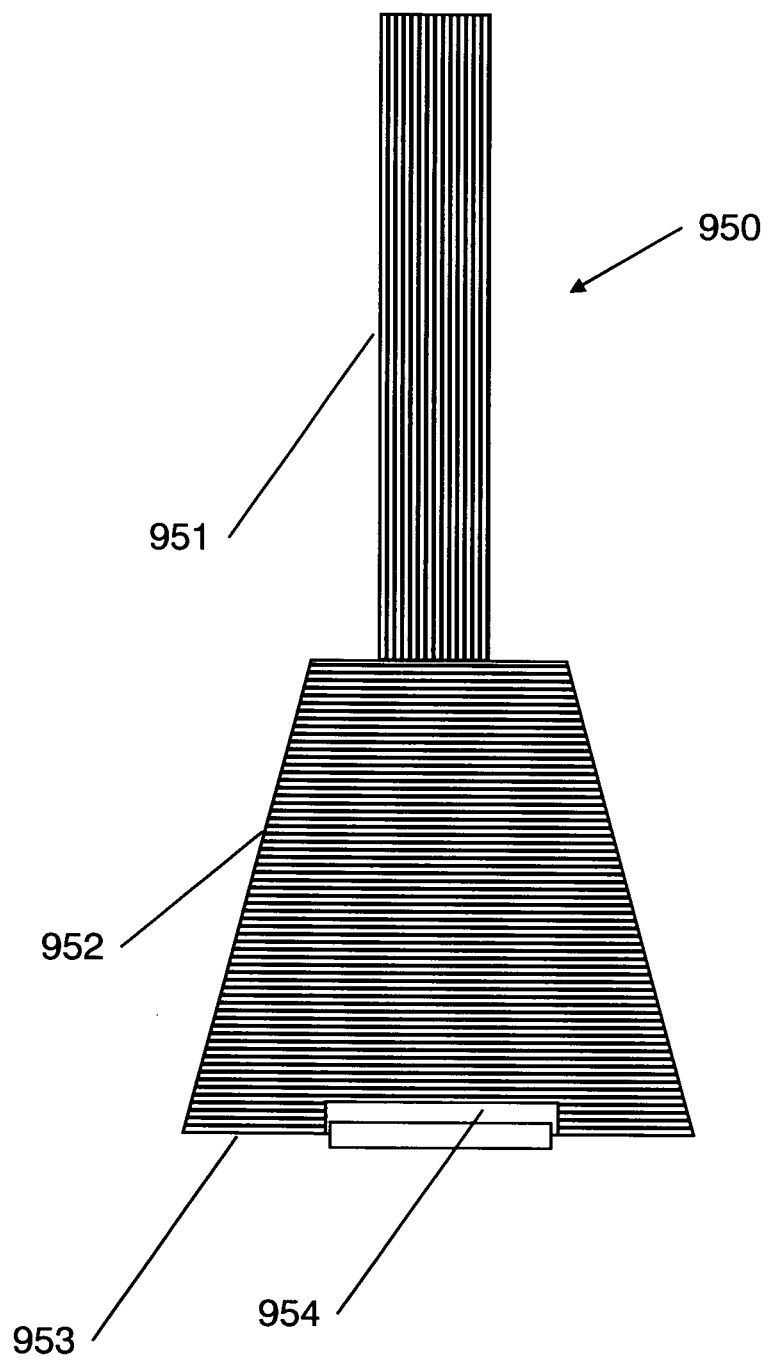

FIG. 3a schematically depicts a disassembled plasma head comprising body and interchangeable tissue welding tip according to an exemplary embodiment of the current invention;

FIG. 3b(i) schematically depict assembled plasma head with interchangeable tips for tissue welding and tissue ablation respectively according to an exemplary embodiment of the current invention;

FIG. 3b(ii) schematically depicts assembled plasma head with interchangeable tips for tissue welding and tissue ablation respectively according to another exemplary embodiment of the current invention;

FIG. 4a schematically depicts a cross section of a plasma welding tip according to an exemplary embodiment of the current invention;

FIG. 4b(i) schematically depicts a cross section of a dual purpose plasma welding and ablation tip in bi-polar welding configuration, according to another exemplary embodiment of the current invention;

FIG. 4b(ii) schematically depicts a cross section of a dual purpose plasma welding and ablation tip in mono-polar ablation or coagulation configuration, according to another exemplary embodiment of the current invention;

FIG. 4c schematically depicts a cross section of a plasma welding tip according to yet another exemplary embodiment of the current invention;

FIG. 4d schematically depicts a cross section of a plasma welding tip using induction activated plasma according to yet another exemplary embodiment of the current invention;

FIG. 4e(i) schematically depicts a vertical cross section of an asymmetric plasma welding tip according to yet another exemplary embodiment of the current invention;

FIG. 4e(ii) schematically depicts a horizontal cross section of an asymmetric plasma welding tip seen in FIG. 4e(i) along the A-A line, according to yet another exemplary embodiment of the current invention;

FIG. 4f schematically depicts a cross section of an asymmetric plasma welding tip, having a bent tube according to yet another exemplary embodiment of the current invention;

FIG. 5a schematically depicts block diagram of optional electrical circuited of a bi-polar plasma system according to an exemplary embodiment of the current invention;

FIG. 5b schematically depicts the electrical connections of a mono-polar plasma system according to an exemplary embodiment of the current invention;

FIG. 6 schematically depicts a miniature plasma welding system according to another exemplary embodiment of the current invention;

FIG. 7a schematically depicts an electric circuit for driving a bipolar plasma head according to an exemplary embodiment of the invention;

FIG. 7b schematically depicts electronic circuit for plasma monitoring, optionally used with the electric circuit for driving a plasma head according to an exemplary embodiment of the invention;

FIG. 8a schematically depicts a plasma welder for deep cut welding according to the current invention;

FIG. 8b schematically depicts another cross-section view of a plasma welder for deep cut welding seen in FIG. 8a according to the current invention;

FIG. 9a schematically depicts the use of two plasma heads for welding of a long stretch of wound according to an exemplary embodiment of the invention;

FIG. 9b schematically depicts the use of two plasma heads and a needle for welding of a long and deep stretch of wound, combines the advantages of deep cut welding of FIGS. 8a,b with the long welding capability by using two plasma heads of FIG. 9a;

FIG. 10a schematically shows a side cross section of a plasma head for welding a long section of cut according to an exemplary embodiment of the current invention;

FIG. 10b schematically shows a top view of the plasma head seen in FIG. 10a according to an exemplary embodiment of the current invention;

FIG. 10c schematically depicts a "downstream plasma" head for efficient welding of large cuts according to an exemplary embodiment of the current invention;

FIG. 11 schematically depicts a side cross section of long plasma head having an RF coil according to another embodiment of the current invention;

FIG. 12 schematically depicts a large plasma head having an external ring electrode and an internal isolated electrode according to an exemplary embodiment of the current invention;

FIG. 13 schematically depicts a plasma head having a spiral central electrode according to an exemplary embodiment of the current invention;

FIG. 14 schematically depicts an ergonometric plasma head according to another embodiment of the current invention;

FIG. 15 schematically depicts a plasma head having stand-off legs for controlling the distance of the plasma head to the treated tissue according to another embodiment of the current invention; and FIG. 16 schematically depicts a wiper for uniformly spreading albumin solution on tissue according to another embodiment of the current invention.

DESCRIPTION OF THE PREFERRED EMBODIMENTS

The present invention relates to an apparatus and method for tissue welding applications using a plasma head.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways.

FIG. 1 schematically depicts a block diagram of plasma welding system for welding tissue according to an exemplary embodiment of the current invention.

According to an exemplary embodiment of the invention, plasma welding system 100 comprises control and supply unit 101 connected to a hand-held plasma head 102 via a flexible hose 122. Control and supply unit 101 supplies to a hand-held plasma head, 102 via a flexible hose 122 at least: gas, which is used for plasma generation, and Radio Frequency (RF) energy, for exciting the gas and creation the plasma 116.

Flexible hose 122 may optionally return to control and supply unit 101 signals indicative of welding process parameters, for example: plasma emission spectra, plasma temperature, tissue temperature, RF current, RF impedance, etc. Additionally, hose 122 may further comprise an electrical cable for transmitting commands from command switches on plasma head to control and supply unit 101.

It should be clear that Flexible hose 122 may comprise a plurality of hoses and may comprise additional tubing, electrical cables, optical fibers, etc. Similarly, it should be clear that control and supply unit 101 may be housed in one or more housing, for example, electronics and gas handling sub-units may be separately housed. Preferably, a compact and portable plasma welding system may comprise a single, compact control and supply unit Gas Supply Sub-System Gas supply sub-system of plasma welding system 100 comprises at least one gas tank 131 holding pressurized gas. In the exemplary embodiment illustrated in FIG. 1, tank 131 is seen situated inside control and supply unit 101; however, tank 131 may be placed outside control and supply unit 101.

Preferably, Helium (He) gas is used due to its low breakdown voltage. Thus, low RF power is needed to produce plasma. Low RF power reduces the size and cost of the RF generator and enables operating the system using battery power, for example using the optionally rechargeable battery 165. Using gas with low breakdown voltage enables working at low plasma temperatures as needed for the welding process. However, other gases or gas mixture may be used. For example Argon (Ar) gas may be used. Specifically, other gases may be used for different applications. For example, low plasma temperature may be advantageous for plasma welding procedure, while other gases may be used for ablation of tissue, cutting tissue or coagulation. In some embodiments, a plurality of gas tanks is used holding different gases or gas mixtures.

Breakdown voltage of gases is given by Paschen's law described by the equation:

$$V = \frac{a(pd)}{\ln(pd) + b}$$

where V is the breakdown voltage in Volts, p is the pressure and d is the gap distance. The constants a and b depend upon the composition of the gas. It can be seen that when working under atmospheric pressure, the breakdown voltage depends on the gas properties and the discharge gap. To reduce the breakdown voltage, the preferred gas chosen is He and the gap between the RF electrodes (or the RF electrode and the ground electrode) is minimized.

In some embodiments, a chemically active gas is used, or a chemically active component or components is added to the gas. For example, a polymerizing gas can be added to the carrying gas to enhance adhesion of the cut sidewalls. An example for such a gas is a high polymerizing gas as CHF3 or CH3F which when disassociates in the plasma enhances C and F polymer chains. Optionally, reactive gas such as O2 is used.

Gas tank 131 may be a replaceable or disposable tank or it may be refilled on site. Preferably, gas tank 131 is equipped with a valve and connecting fitting 132 and is connected to a pressure reducing regulator 133. Regulator 133 reduces the gas high pressure in the tank to lower pressure, for example 20 to 30 psi.

Preferably, optional Mass Flow Controller (MFC) 134 is used to ensure constant and known gas flow. MFC 134 may be mechanical or electronic and is optionally controlled by controller 161 in the supply and control unit 101.

Electric solenoid valve 135 optionally controlled by controller 161 opens to allow gas flow from the gas subsystem, through gas conduit 137 to flexible hose 122.

Optionally, flexible hose is removably connected to the supply and control unit 101 by connector or plurality of connectors 104 such that several, or several types of hand held plasma heads 102 may be used with the same supply and control unit.

It should be noted that components of the gas supply sub-system may be manually controlled instead of electronically controlled by controller 161.

It was experimentally found that gas flow rate of 1 Liter per minute at 1 atm., or even substantially less, is sufficient for maintaining the plasma. Thus, a gas tank of 150 cc volume, pressurized to 200 atm. will last 30 minutes of continues operation. Such gas tank is small enough (for example a cylinder of 2 cm inner radius and 12 cm inner length) to be fitted in a compact portable unit which may be carried and used in the field. Alternatively, large gas tank may be used in stationary unit or in a unit mounted on a cart.

According to a preferred embodiment of the current invention, system 100 may be housed in a box having approximately 40×40×20 cm dimensions, wherein the plasma head is a hand held pen-like applicator connected with a hose of 1 to 2 m long.

RF Sub-System

Supply and control unit 101 further comprises an RF sub-system for supplying Radio Frequency (RF) power for igniting and maintaining the plasma.

The RF sub-system preferably comprises an RF generator 141 followed by amplitude modulator 142. Optionally, frequency of an RF generator 141 and modulation parameters such as: modulation depth, shape and frequency of amplitude modulator 142 are controlled by controller 161. It should be noted that modern RF generators may perform both RF generation and modulation. RF signal is then amplified by RF amplifier 143 which may also be controlled by controller 161. Alternatively, pulsed DC power may be used.

Electrical power is preferably coupled to the RF input line 147 through optional impedance matching circuit 144. Preferably, RF input line 147 is a coaxial electric cable. In some embodiments, plasma is produced in "bi-polar" mode, wherein RF circuit is completed by plasma created between two closely spaced electrodes at the tip of plasma head 102.

Preferably, a grounding electrode 145, connected is attached to the patient's skin, for example to his/her hand, or attached in proximity to the plasma treated zone. Grounding electrode 145 is connected to the RF sub-system via electric cable 146. Grounding the patient is both a safety measure and it allows using the plasma head in "mono-polar" mode, wherein RF electric circuit is completed through the patient's tissue, grounding electrode 145 and electric cable 146.

According to an exemplary embodiment of the current invention RF frequency higher than 100 KHz is used, for example 1 to 20 MHz. Preferably a frequency of approximately 4 MHz is used, however lower or higher frequency may be used. According to an exemplary embodiment of the invention, RF power 0.5 to 15 Watt is used. This power level allows both tissue welding and tissue etching at a rate of 1 to 50 mm/min, however higher or lower power levels and ablation rates may be used for higher or lower rates.

Preferably, RF signal is modulated for enhancing the plasma ignition and maintenance efficiency while keeping the plasma characteristics of the carrier wave. For example plasma is generated with a carrier wave frequency of 4 MHz and 99% modulation of 1000 Hz. The plasma thus produced is "non-arcing" plasma as expected from a 4 MHz frequency but is ignited and sustained by an RF power significantly lower than needed without the modulation. However, different modulation depth or, modulation frequency and modulation envelope shape may be selected.

Plasma Control

Impedance matching circuit 144 matches the dynamic impedance of the circuit which changes according to the plasma impedance (which varies according to the plasma conditions). Additionally, RF power level may be controlled for example by: changing the gain of amplifier 143, by using modulator 142 as an attenuator; or changing the RF power generated by generator 141. Optionally, modulation parameters and RF frequency may be changed in response to changing plasma behavior, response of the tissue or welding compound, medical procedure, etc.

Optionally, signals extracted from electric cable 169 may be used for controlling the plasma as will be explained later.

Similarly, signals extracted from impedance matching circuit 144, via electric connection 148 may also be used for controlling the plasma. Optionally, in some embodiments, processor 161 receives signal indicative of plasma process, for example by monitoring electrical plasma current or plasma impedance, for example through monitoring line 148. In some embodiments, impedance matching circuit 144 comprises a resistor and voltage developed on said resistor is indicative of plasma current. In some embodiments, said resistor is situated within the plasma head. In some embodiments, in close proximity to the plasma electrode.

Optionally control and supply unit 101 further comprises an optical spectrometer 151. Spectrometer 151 receives light generated by plasma 116 via optical fiber 152. Optional optical fiber 152 delivers optical signals generated by the plasma 116 and indicative of the strength of the plasma and its stability, as well as ablation/welding products of said plasma to the optional optical spectrometer 151. Electrical signals from spectrometer 151 are reported to controller unit 161 and are used for analyzing the progress of the plasma welding or ablation. Optionally, spectrometer 151 comprises one or a plurality of optical filters and optical sensors.

For example, optical spectrometer 151 may detect the abundance of phosphorus (P) in the living cells which does not exist in the fat tissue, for example by monitoring one of the phosphorus wavelengths, for example at 253 nm.

Additionally or alternatively, other optical sensors (not seen in this figure) may be installed within plasma head 102 and be used for monitoring the welding or ablation progress. Said sensors receive power and report their reading to controller 161 through electric cable 169.

Controller

Controller unit 161 may be a computer such as a PC or a laptop computer. However, controller 161 may be a DSP or other data processing device. Controller 161 receives user input and display user output through peripherals units 162 which may comprise some of: keyboard, mouse, foot pedal, and/or other input devices, a display, printer, loud speaker and/or other output devices, and optionally external storage devices and LAN or internet communication. Additionally, controller 161 may receive commands from optional user input devices 113 located on plasma head 102 via electric cable 169.

It should be noted however, that components of the RF sub-system may be manually controlled instead of electronically controlled by controller 161. In such embodiments, controller 161 may have limited function or missing.

In the case of a Portable device, the RF system is miniaturized using solid state devices to generate the RF and to control the process. With average RF power of 5 W, Energy conversion efficiency of 33.3% of the amplifier, and low energy consumption of the controller, generator and sensor, for example a standard Lithium 9V battery 165, having capacity average of 1200 mAh should last for 30 min. Thus, battery size is compatible with compact portable unit. In some embodiments, battery 165 is a rechargeable battery while in other embodiments, battery 165 is replaceable, and in yet other embodiments, power is supplied by plugging the power outlet.

Plasma Head

According to an exemplary embodiment of the current invention, the plasma welding unit comprises a plasma head 102 connected to control and supply unit 101 connected to a hand-held plasma head 102 via a flexible hose 122. Typical dimensions for the pen-like plasma head 102 may be a length of approximately 15 cm and diameter of 1 to 2 cm.

In some embodiments, hose 122 is permanently connected to the control and supply unit 101, however, in other embodiments, hose 122 may be detached from control and supply unit 101 at hose connector 104. It should be noted that connector 104 may comprise a plurality of connectors for: gas supply tubing, RF line, electronic cable, and the optical fibers. Preferably, connector 104 is a quick release connector enabling to quickly replace the hose and the plasma head. Replacing plasma head may be useful for changing type of head, and for replacing the head with a new sterile head before each procedure. Optionally the hose and head are disposable. Alternatively, hose and head are sterilizable. In some embodiments the hose is connected to the head using a connector so that only the head is replaceable. In yet other embodiments, only the tip assembly 114 of the plasma head is replaceable.

Plasma head 102 comprises a body 112, adapted to be hand held. Optionally head 102 comprises control switch or switches 111 which are used by the operator for controlling the operation of system 100, for example by turning on or off or adjusting the gas flow, turning on or off or adjusting the RF power, providing composition for tissue welding, etc. Additionally, head 102 optionally comprises indicator or indicators 113, such as LEDs indicating status of system 100, for example gas flow, RF power, etc.

Additionally, plasma head 102 may comprise an injector 118 for injecting composition 250 for tissue welding, for example albumin solution which may be injected into a gap, cut or a discontinuation 260 in the tissue 270 and used as solder when activated and solidified by the plasma. Injector 118 preferably injects the tissue welding composition through a nozzle 119 which preferably terminates near the distal end of plasma tube 115. Optionally, the injector is located outside the body 112 of plasma head 102, and nozzle 119 is connected to a tube leading to the injector. In some embodiments, the injector is located within the supply and control unit 101, and is optionally activated using one of the switches 111.

FIG. 2 schematically depicts some details of a hand held plasma head 102 for plasma welding according to an exemplary embodiment of the current invention.

In this figure, the components of hose 122, namely gas line 137, optical fiber 152, RF cable 147 and electric cable 169 are seen separately, however it should be noted that preferably all these components are housed within a common flexible shroud.

In the depicted embodiment, injector 118 is attached to, or housed inside body 112 of head 102. For example, injector 118 may be a syringe with albumin solution having a spring loaded piston 230. Injector 118 is connected to nozzle 119 via solder tube 219 interrupted by mechanical or electrical valve 211 such that opening valve 211 enables application of tissue welding compound through nozzle 19 to the tissue to be welded.

Alternatively, the injector 118 may be mechanically or electrically activated to supply a predetermined amount of welding compound when it is activated. Optionally, injector 118 may comprise an electrically activated pump configured to supply welding compound at predetermined rate when it is activated.

In a proffered embodiment of the current invention, the composition 250 for tissue welding is albumin solution. Preferably, high concentration Albumin is required. Albumin may be purchased from an albumin supplier, for example from Sigma-Aldrich or Equitech-Bio, in a powder state. The albumin is mixed with sterile water to the concentration needed, for example 50% w/v.

Only small amount of albumin is needed, for example a 5 cm cut may require 5 grams of albumin at cost of $0.5 to 2.5 per gram, depending on the amount purchased.

The use of albumin as a "biological glue" is based on an albumin which when is being activated, gets denaturized and "sticks" to the surfaces in vicinity. Most of the data about using albumin as "glue" was gathered during 15 years of research done on tissue soldering using laser.

Albumin refers generally to any protein with water solubility, which is moderately soluble in concentrated salt solutions, and experiences heat coagulation (protein denaturation). The most well-known type of albumin is the serum albumin in the blood. Serum albumin is the most abundant blood plasma protein and is produced in the liver and forms a large proportion of all plasma protein. The human version is human serum albumin, and it normally constitutes about 60% of human plasma protein.

Most used albumins for soldering applications (laser) are bovine serum albumin—BSA (cattle) and human albumin. The albumin before denaturation is formed mainly in $\alpha$-helix structure. It is assumed that the chemical arrangement is based mainly on electrical bond (hydrogen bonds) which gives the electric potential used by the plasma an important role.

Optionally, "custom made" albumin may be developed and fitted to the plasma process characteristics.

Optical fiber 152 preferably terminates at distal end 252 located near the distal end of plasma tube 115 so that light generated by plasma 116 enters the distal end 252 of the optical fiber 152. Optionally, distal end 252 of the optical fiber 152 comprises light collection optics (not seen in this figure for clarity) for enhancing light collection efficiency and increasing signal of spectrometer 151. One problem encountered during tissue welding is overheating and even charring of the welding area. Using spectrometer 151 for monitoring the welding process may insure that the temperature stays within the safe limits.

FIG. 3*a* schematically depicts a disassembled plasma head 102 comprising body 112 and interchangeable tissue welding tip 300W according to an exemplary embodiment of the current invention.

In this exemplary embodiment, interchangeable tip 300W is comprises connector 314W and plasma welding tube 315W. Connector 314W connects gas conduit and RF cabling in body 112 to gas channel and RF electrodes in plasma welding tube 315W. Preferably, the connection is a quick release type. For simplicity, fiber optic connection is not seen in this figure. However, optional optical fiber 152 may simply extend from body 112 for example trough a slit in connector 314W. Alternatively, an optical connector may be used with a short section of fiber. Alternatively, plasma welding tube 315W is made of transparent material such as glass, quartz, sapphire etc, and used for light collection instead of the last section of fiber 152. In this case, collected light may be confined in the transparent tube by total internal reflection, as in clad-less fiber, or a light reflecting layer may be added to the side of the tube, for example metallic or dielectric reflective coating. Light thus collected is transferred to the optical fiber in body 112. For simplicity, nozzle 119 is not seen in this figure.

It should be noted, that mating interfaces 398 and 399 on body and tip respectively may comprises of electrical connection such as contacts or plugs for transmitting electrical signals between the body and tip, gas connection that may comprise "O" ring or other gas seal, and fasteners to join the two parts.

FIGS. 3*b*(*i*) and 3*b*(*ii*) schematically depicts assembled plasma head with interchangeable tips 300W and 300A for tissue welding and tissue ablation respectively according to an exemplary embodiment of the current invention.

In tip 300W for tissue welding, plasma 116 is created using bi-polar electrodes within tube 315W.

In contrast, tip 300A for tissue ablation is quipped with preferably needle shaped, mono-polar ablation electrode 315A. Alternatively, mono-polar ablation electrode 315A may be scalpel shaped or has other shape. Plasma 116 is produced by RF current flows from ablation electrode 315A to tissue 270 which is grounded via grounding pad 145 and grounding cable 146. In this embodiment, plasma tube is missing. When ablation is performed, the plasma don't necessary exist. Ablation is usually performs without gas flow, and the RF just ablate the tissue by hyperthermia. Alternatively, atmospheric air may be ionized to plasma during RF ablation.

In this embodiment, last section of optical fiber 152 may also be missing.

In some embodiments nozzle 119 is removable and is removed, optionally with injector 118, solder tube 219 and valve 211, when changing to ablation configuration. Alternatively, injector 118, solder tube 219 and valve 211 stay on body 112 and only the nozzle is removed. Yet alternatively, nozzle 119 is part of welding tip 300W, connecting to solder 219 via a tube fitting and is removed with it when changing configuration.

Optionally or alternatively, system 100 comprises a plurality of hoses and plasma heads connected to one supply and control unit 101. For example, an ablation head and welding head may be provided such that the user can use one or the other without having to reconfigure the heads.

FIG. 4a schematically depicts a cross section of a plasma welding tip 400 according to an exemplary embodiment of the current invention.

For simplicity, non essential details (some already depicted in other drawings) are not depicted in this figure.

Tip 400 comprises a base 401, capable of connecting to body 112 of a plasma head. Preferably, using a quick release connector preferably having a fastener (not seen in this figure) to hold the tip in place. Tip 400 receives RF power from RF (optionally a coaxial) cable in body 112 via contacts 412 and 411. Preferably, contact 412 is connected to the central conductor of the RF cable, while contact 411 is connected to the outer conductor of said coaxial cable. Additionally, tip 400 receives gas flow 406 from gas tube in body 112 of plasma head via gas input opening 405 of central gas tube 416.

Central gas tube 416 is preferably thin metallic tube that acts also as central electrode for bi-polar plasma production. Preferably, central tube is sharpened and optionally serrated at its distal end 417 to enhance plasma production and reduce the voltage needed for ionization. Central tube 416 is held centrally to outer tube 409 using spacer 418. Outer tube 407 is preferably a thin wall tube made of non-conducting material such as glass, ceramics, plastic or quartz. A transparent outer tube enables easy visual confirmation of the plasma ignition. An annular RF grounding electrode 414 is connected to the RF cable in body 112 via return line 413 and contact 411. It should be noted that while return line 413 is seen in this figure on the outside of outer tube 404, it may be positioned inside said outer tube as long as it is properly insulated from inner tube 416.

FIG. 4b(i) schematically depicts a cross section of a dual purpose plasma welding and ablation tip 420 in bi-polar welding configuration, according to another exemplary embodiment of the current invention.

For simplicity, non essential details (some already depicted in other drawings) are not depicted in this figure. For simplicity, some parts that were already explained may not be marked in this figure.

Tip 420 comprises a base 401 (not marked in the figure), capable of connecting to body 112 of a plasma head. Preferably, using a quick release connector preferably having a fastener (not seen in this figure) to hold the tip in place. Tip 420 receives RF power from RF (optionally a coaxial) cable in body 112 via contacts 422 and 421. Preferably, contact 422 is connected to the central conductor of the RF cable, while contact 411 is connected to the outer conductor of said coaxial cable. Additionally, tip 420 receives gas flow 406 from gas tube in body 112 of plasma head via gas input opening 425 which is opened to lumen of outer tube 431.

In contrast to tip 400, tip 420 comprises a central electrode 426 instead of central gas tube 416. Central electrode 426 is preferably thin metallic rode acting as the central electrode for bi-polar plasma production. Preferably, central electrode is sharpened at its distal end 427 to enhance plasma production and reduce the voltage needed for ionization. Central electrode 426 is held centrally to outer tube 431 using spacer 428 having openings 429 to allow gas flow 430. Outer tube 431 is preferably a thin wall tube made of non-conducting material such as glass, ceramics, plastic or quartz. A transparent outer tube enables easy visual confirmation of the plasma ignition. Similarly to tip 400, an annular RF grounding electrode is connected to the RF cable in body via return line and RF connector contact 421. It should be noted that while the return line is seen in this figure on the outside of outer tube 404, it may be positioned inside said outer tube as long as it is properly insulated from inner tube 416.

FIG. 4b(ii) schematically depicts a cross section of a dual purpose plasma welding and ablation tip 420 in mono-polar ablation or coagulation configuration, according to another exemplary embodiment of the current invention.

For simplicity, non essential details (some already depicted in other drawings) are not depicted in this figure. For simplicity, some parts that were already explained may not be marked in this figure.

As depicted in this figure, central electrode 426 is pushed forward, using a mechanical lever or an electrical solenoid optionally located within body 112 of plasma head (not seen in this figure), until its distal end 427 is outside outer tube 431. In this configuration, RF circuit is completed via grounding pad 145. Preferably, RF power to annular grounding electrode 434 is turned off. However, central electrode 426 may be insulated along it length and exposed only at its tip 427. In this case, most of the current will flow through pad 145 even if annular electrode 434 is connected to the RF circuit.

FIG. 4c schematically depicts a cross section of a plasma welding tip 440 according to yet another exemplary embodiment of the current invention.

For simplicity, non essential details (some already depicted in other drawings) are not depicted in this figure. For simplicity, some parts that were already explained may not be marked in this figure.

In contrast to tip 400 of FIG. 4a, gas flow 442 flows in the lumen created between central tube 444, which is also used as central electrode and outer tube 446. Central tube 444 is held centrally to outer tube 446 by spacer 448 having openings 449 for gas flow 442.

Optionally, annular grounding electrode 450 is wide to create a large overlap with distal end 452 of central tube 444.

FIG. 4d schematically depicts a cross section of a plasma welding tip 460 using induction activated plasma according to yet another exemplary embodiment of the current invention.

For simplicity, non essential details (some already depicted in other drawings) are not depicted in this figure. For simplicity, some parts that were already explained may not be marked in this figure.

In contrast to tips 400, 420 and 440, RF power supplies to tip 460 via contacts 462 and 463 is connected via lines 465 and 466 to a coil 467 wound around outer tube 469. Coil 469 is preferably part of a tuned resonance circuit which may be a part of the impedance matching circuit. Alternatively, coil 469 acts as an RF antenna, not connected at its distal end) RF current in coil 467 excites the gas flow 470 in outer tube 469 and thus creates plasma. In some embodiments, number or turns in coil 469 is limited, for example only few turns, and optionally as few as 1, 1.5 or 2 turns.

In this configuration, gas flow 470 in outer tube 469 is uninterrupted, thus larger flow may be achieved, or thinner tube may be used. Although lines 465 and 466 and coil 467 are seen on the outer side of outer tube 469, it should be noted the any of them can be placed on the anterior of said tube.

FIG. 4e (i) schematically depicts a cross section of an asymmetric plasma welding tip 480 according to yet another exemplary embodiment of the current invention.

For simplicity, non essential details (some already depicted in other drawings) are not depicted in this figure. For simplicity, some parts that were already explained may not be marked in this figure.

Asymmetric plasma welding tip 480 is shown in this exemplary embodiment as having plasma excitation electrode configuration similar to tip 420 seen in FIG. 4b(i). However, other plasma excitation configurations, for example that of tip 400, 440 or 480 may be used.

In contrast to tips 400, 420, 440 and 460, outer tube 482 is closed at its distal end 484, and has a side opening 486 through which plasma 488 exits as it pushed by gas flow 490. Alternatively, plasma may be generated in a mono-polar way between the electrode 426 and the tissue, but sideways through opening 486.

Preferably, cross section of outer tube 482 is oval having its long axis in the direction in which plasma 488 exits opening 486 in outer tube 482 as can be seen in FIG. 4e(ii) which shows a transverse cross section along the plane A-A of FIG. 4e(i).

In a preferred mode of operation, tip 480 is moved in the direction 492, opposite to the plasma exit opening 486 within a narrow gap to be welded while the plasma welds the gap behind the tip.

It also should be noted that albumin solution or other biologic glue may be supplied to the gap in the tissue through any of the lumens in tips 400, 420, 440, 460 or 480. In some embodiment gas pressure is used for pushing the glue towards the tissue and possibly for clearing the lumen before plasma ignition.

FIG. 4f schematically depicts a cross section of an asymmetric plasma welding tip 490, having a bent tube according to yet another exemplary embodiment of the current invention.

Asymmetric plasma welding tip 490, having a bent outer tube 495 is similar to any of previously depicted tips, however outer tip 495 is bent 494 such that opening 497 is not in line with the long axis of the plasma head, the tip or the outer tube. In the depicted embodiment, a 90 degrees bent 495 is depicted, however, smaller bending, for example 20 to 80 degrees are possible. Optionally, the diameter or cross section may be different than the length of the tube. Using bent tip may be advantageous for reaching hard to access tissue, or when operating within a cut.

Electrode assembly may be situated within the bent part 496 of the outer tube, or near its opening 497. It should be noted that the bi-polar plasma production assembly seen in FIG. 4f is exemplary, and Asymmetric plasma welding tip 490 may comprise other plasma production configuration, for example other types depicted in this application or known in the art.

FIG. 5a schematically depicts block diagram of optional electrical circuited of a bi-polar plasma system according to an exemplary embodiment of the current invention.

This configuration may be used primarily with tissue welding plasma head such as tissue welding tip 300W.

Optional variable impedance 511 is placed in the RF electrical return line. When the impedance of variable impedance 511 is low, electrical return current is flowing primarily from central electrode 530 through ground electrode 525. Thus, the device acts as mainly bi-polar.

In contrast, when the impedance of variable impedance 511 high, the electrical return current is flowing primarily from central electrode 530 to patient's body 270 and returning via grounding electrode pad 145 electrically connected through grounding cable 146. Thus, the device acts as mainly mono-polar. When the impedance of variable impedance 511 intermediate, the device acts as a combination of bi-polar and mono-polar.

An RF forward and backwards power measurement may be done by the standard devices (dual directional coupler) which are here assumed to be part of the impedance matching circuit 144. The forward power is monitored and passes a signal to the generator power control. When the forward power exceeds a certain power (for example 10 W), the generator decreases the power and maintain a maximum power as preset.

When the patient body, electrically grounded to grounding pad is closer to the plasma tip, the plasma impedance is lower, and the power that the plasma absorbs is higher and thus the forward power shows higher readings, (or the impedance which is monitored becomes lower) this may be feedback to the controller to regulate the power to the lower power preset. An alternative possible control method, experimentally demonstrated, is "plasma current measurement" wherein a wire loop around the plasma senses the charge that passes in the plasma and points on the plasma density and plasma power.

FIG. 5b schematically depicts the electrical connections of a mono-polar plasma system according to an exemplary embodiment of the current invention.

This configuration may be used primarily with tissue ablation plasma head such as tissue ablation tip 300A.

Electrical return current is flowing from ablation electrode 530 to patient tissue 270 and returns through grounding pad 145 electrically connected to the patient's body. Thus, the device acts as mono-polar. Mono-polar plasma 116 then ablates tissue 270 creating a cut 560.

It should be noted that bi-polar tip and electrical circuit may act as mono-polar tip and electrical circuit by changing the characteristics of variable impedance 511, forcing the RF electrical circuit to close through grounding pad 145. Optionally, ablation however may be performed with a contact of electrode 530 to the tissue.

Optionally, central electrode 530 (FIG. 5a) may be slide towards the tissue (or tube 315W retracted toward the plasma head body 112), to expose the central electrode 530 when mono-polar ablation or coagulation action is needed. It should be noted that welding action and ablation or coagulation may require different RF parameters such as frequency, power and modulation.

FIG. 6 schematically depicts a miniature plasma welding system 600 according to another exemplary embodiment of the current invention.

Miniature plasma welding system 600 comprises a body 601 holding all the essential elements of control and supply unit 101.

Body 601 holds at least a miniature gas tank and gas supply subsystem. Gas subsystem in body 601 may optionally be simplified, for example it may comprise a rudimentary flow controlling devices, for example based on flow restricting orifice, optionally capable of providing fixed flow only. For example, rudimentary gas flow subsystem in body 601 may comprise only mechanical elements, or constructed without gas flow sensors.

Body 601 additionally comprises a battery for operating the RF subsystem for a limited duration. RF subsystem in body 601 is miniaturized. Similarly, controller in body 601 is absent, or is of a rudimentary construction. For example, input/output devices are restricted to few input keys and few LED indicators and/or a small LCD display.

Optionally, the spectrometer is missing from body 601.

Tip 114 is preferably connected directly to body 601, thus hose 122 is not needed. Tip 614 may be any of the previously shown tips, including ablation type tips.

Optionally, glue supply system 660 is attached to, or incorporated within body 601 of miniature plasma welding system 600.

Controls 612 on body 601 activate gas flow and RF power. Optional wire 666 may be connected to an optional grounding pad 145. It should be noted that when miniature plasma system is battery operated, grounding the patient may not be necessary. However, grounding pad 145 may be used for mono-polar operation and plasma feedback.

FIG. 7a schematically depicts an electric circuit 700 for driving a bipolar plasma head according to an exemplary embodiment of the invention.

Bipolar isolator 701 is inserted between RF amplifier 143 and RF cables 705 and 706 leading to a first and a second electrode (for example electrodes 417 and 414 of FIG. 4a), or to the coil (for example coil 467 in FIG. 4d). It should be noted that isolator 700 may replace, or be a part of impedance matching unit 144.

As a result, the RF voltage is floating by using the transformer 704 with respect to the ground (patient's body potential) 703 and is thus between one electrode to another. This causes the plasma to be directed from the first to the second electrode and not to the ground (the patient's body) as in a uni-polar configuration.

This optional embodiment may enables determining the electric current flow of direction and instead of flowing through the patient's body to the ground electrode (as in uni-polar), it flows to the second bipolar electrode which can be inserted at a desired location.

An optional variable load such as a variable resistor 707 between the source and one of the electrodes differentiate the power transferred to the electrodes and enables transferring more power from one electrode than the other by "wasting" power on the load.

Optionally plasma parameter monitor 709 is inserted in line with the output 701 of RF amplifier 143.

Alternatively, isolator 701 and/or monitor 709 are inserted after, or integrated into impedance matching circuit 144 as seen in FIG. 1.

FIG. 7b schematically depicts electronic circuit for monitor 709. In this electronic schematic, meters 710 and 711 showing transmitted and reflected power respectively receives signals from sensing coil 712.

In an exemplary embodiment of the invention, signals indicative of transmitted and/or reflected RF power are optionally digitized and transferred to processor 161 via line 148 as seen in FIG. 1 and are used for plasma monitoring and control.

By knowing the transmitted and reflected RF power it is possible to know the power deposited in the plasmas and to deduct the impedance of the treated surface or the distance to ground. If the distance to ground is known and constant, the only free parameter is the surface conductivity which is indicative of the albumin denaturation state.

For example, increase of the impedance may be indicative of dehydration of the albumin after it already been crossed linked by the plasma. In this case, the plasma may be turned off to prevent thermal damage to the tissue.

FIG. 8a schematically depicts a plasma welding system 720 for welding deep cut such as cut 722 according to the current invention.

Deep cut 722 may be deeper than 3 mm below the skin surface 727, penetrating below the epidermis layer 724, and may be into the subcutaneous structures 725. These types of cuts, which are common for example in surgery, may be difficult or impossible to weld using standard uni-polar welding techniques.

In an exemplary embodiment of the invention, a bi-polar plasma is used. Bi-polar plasma is created between a first electrode 719 and a second electrode 721. First electrode 719 is preferably in a plasma head such as one of the plasma tips disclosed herein, for example tip 300, 400, 460, etc. Second electrode 721 is inserted deep into cut or incision 722.

As in the uni-polar case, first electrode 719 consists of a plasma head which generates plasma (gas ionized by the RF energy). Second electrode is buried inside the incision before welding. The solder (albumin) is injected above/on the second electrode 721 in a way that it fills the incision.

Second electrode 721 has a narrow shape of a needle or a wire and can be removed after the welding process. Turning it while removing may help removal.

When plasma is applied, the electric current flows from the plasma head 719 to second electrode 721 and while doing so, heats the solder in its way (joule heating) and denaturizes it.

This embodiment enables a deep welding up to 3 mm and more (which can't be achieved in a uni-polar configuration).

When the cut is long, the plasma head is moved along the cut during welding. In very deep cuts, the lower part of the cut is welded first, and than the second electrode is pulled and inserted above the welded section, a second layer of albumin is applied and the welding process repeats until the full depth of the cut is welded.

FIG. 8b schematically depicts a side cross section of plasma welding system 720 seen in FIG. 8a showing the preferably synchronously motion direction 729 of first electrode 719 and second electrode 721 according to the current invention.

FIG. 9a schematically depicts a welding system 730 using two plasma heads 731 and 732 for welding of a long stretch of wound according to an exemplary embodiment of the invention. The figure is a cross section along the length of the cut to be welded.

Two plasma head 731 and 732, each may of a type disclosed herein, generates plasma 116 one towards the other.

When directing the two plasma sources to the patient body or albumin, the plasma is ignited at the two sources and RF current flows from one plasma source to the other through the patient body or the albumin.

The media between the plasma sources is heated due to the current flow 734 due to joule heating.

The two heads are preferably positioned close enough to the body so the RF voltage is high enough between them and the body. In some embodiments. Each plasma head has only one electrode and the two heads receive RF voltage at 180 deg phase shift between them in a bi-polar configuration.

When the cut is long, the plasma heads are moved along the cut. In some embodiments, plasma head 719 and electrode 721 may be connected together and are moved together.

FIG. 9b schematically depicts a system 740 for welding deep long cuts according to an exemplary embodiment of the current invention. System 740 combines the advantages of deep cut welding of FIGS. 8a and 8b with the long welding capability by using two plasma heads of FIG. 9a. The figure is a cross section along the length of the cut to be welded—at 90 degrees to the direction of the cross sections in FIG. 8a.

Each plasma heads 741 and 742 may be of the types disclosed herein. In an exemplary embodiment, each of heads 741 and 742 has a single electrode respectively. A third electrode 744 is placed within the wound. Voltage on third electrode 744 may be set in a way that the polarity is opposite to one plasma source or both sources enabling current flow towards it. The polarity of all sources can be switched while processing thus changing the current flow passes as desired.

Optionally, when the cut is long, the plasma heads 741, 742 and third electrode 744 are moved along the cut in the direction 749. In some embodiments plasma heads 741, 742 and third electrode 744 may be connected together and are moved together.

FIG. 10*a* schematically shows a side cross section of a plasma head 750 for welding a long section of cut according to an exemplary embodiment of the current invention.

FIG. 10*b* schematically shows a top view of the plasma head 750 of FIG. 10*a*.

Long plasma head enables a fast welding of long stretch of cut at once, and induces a high electric current flow which heats the albumin faster and better.

The long plasma source can be used in a mono-polar or bipolar fashion.

In mono-polar operation, the patient's body is grounded and acts as a second electrode.

When a bipolar configuration is used, a second electrode is inserted into the cut as seen in FIGS. 8*a,b* and 9*b*.

According to an embodiment of the invention, plasma head 750 comprises a gas input pipe 751 receiving input gas flow 752. The gas flow spreads 756 in funnel like upper flow chamber 753. Top flow chamber 753 is separated from the rectangular bottom gas flow chamber 754 by perforated gas shower plate 755 which acts as a first plasma electrode. Plasma shower 758 is created by RF power supplied from impedance matching 144 to the first electrode 755 and the patient which is grounded by grounding electrode 145. The plasma 758 exits the bottom gas flow chamber 754 which is open at the bottom and heats the albumin in the cut.

The shower plate has many small holes 759 for the gas flow. The holes diameter in the shower plate may be varied according their location in order to achieve a good uniformity of the gas flow along the welding area.

The structure material is preferably heat resistant insulator such as plastic or glass, and the shower plate which made of conductive material such as metal. Preferably the structure is made of transparent material such that the cut, and/or the plasma could be seen. Preferably the material can withstand heat up to, or above 150° C.

FIG. 10*c* schematically depicts a downstream plasma head 770 for efficient welding or disinfection of large cuts or wounds according to another exemplary embodiment of the current invention.

In this embodiment, the gas flow upper chamber 773 comprises at least one first internal electrode 771 for creating plasma 776 within the upper funnel like gas flow chamber 773. The plasma 776 exit 778 towards the cut through the holes in the conductive shower plate 775 that acts as a second electrode. Plasma 778 traverses the lower flow chamber 774, which is open on both upper and lower ends, and heats the albumin in the cut or disinfects the surface.

Optionally, the patient is grounded using grounding plate 145. In these cases, plate 145 may be grounded while RF power is applied only between electrodes 771 and 775. Alternatively, plate 145 may be connected to have the same potential as internal electrode 771, thus attracting plasma 778 towards the patient.

Optionally Electrode 771 is in a form of a coil around the input gas in pipe 751, or optionally, combination of a coil and an internal electrode.

For example, electrode 771 of FIG. 10*c* may be replaced with a coil antenna, acting to ignite plasma. The coil may be placed around the gas in pipe, near the entrance of the gas flow funnel. The coil may be placed outside and around the gas pipe, or inside the pipe. Alternatively, the coil can be inside or outside the gas flow funnel, near the entrance of the gas pipe. The coil may be connected at one side to the RF signal, or may be connected on both sides. If the coil is connected to RF signal on both sides, RF impedance matching circuit is preferably used.

Optionally, the patient is grounded, or connected to the RF signal (as seen for example in FIGS. 1, 5*a*, 6, etc.) to induce plasma flow to the cut.

Optionally, an electrode is placed in the deep cut, to induce current through the albumin as in FIGS. 8*a,b* and 9*b*.

FIG. 11 schematically depicts a side cross section of long, inductively excited plasma 790 head having an RF coil 791 according to another embodiment of the current invention.

In contrast to the embodiments of FIG. 10*a-c*, and similar to the embodiment of FIG. 4*d*, an RF coil 791 is wound around the lower gas flow chamber 794, near the location of the insulating gas shower plate 795.

In one embodiment coil 791 is connected at one end to the RF signal and acts as an electrode. Optionally, the coil may be connected at both ends to the RF signal, as seen in FIG. 11 and inductively excite the plasma 798. In this case impedance matching electronics is preferably used.

The shower plate is sized to fit in the bottom chamber or between the bottom chamber and the upper chamber (gas funnel).

The plasma heads of FIGS. 8-11 may be configured to be implemented as tips to body 112, or may be connected in other ways to system 100.

The following dimensions of plasma heads 750, 770 and 790 as seen for example in FIGS. 10*a* and 10*b* should be viewed as non limiting examples.

The structure: upper and lower flow chambers and gas input pipe is made of material with thickness of approximately 1 mm.

Outer dimensions of lower gas chamber may be: length of approximately 20 to 80 mm; width of approximately 6 to 7 mm; and height of approximately 5 mm.

The thickness of the shower plate is approximately 1 mm and its dimensions are such that it fits within the upper part of the lower gas flow chamber. Optionally a 0.5 mm notch in the walls of the chamber holds the plate in place. The holes are approximately 1 mm in diameter and are approximately equally spaced with approximately 1 mm distance from one hole to the next.

Outer diameter of input gas pipe is approximately 3 mm.

The base of the upper gas flow chamber is approximately the same as the size of the top of the lower gas chamber and its height is approximately 5 mm.

FIG. 12 schematically depicts a large plasma head 800 according to an exemplary embodiment of the current invention.

Plasma head 800 receives gas through input gas pipe 801 and RF power through wires 802 and 803. Optionally, wires 802 and 803 terminates in a connector, and optionally gas pipe 801 is also detachable such that large plasma head 800 can be disconnected and replaced.

Plasma head 800 comprises a tube 805, preferably made of thin glass and having a diameter of 6 to 10 mm. Gas from pipe 801 enters tube 805 through opening 809 and exit through distal opening 810 as plasma directed towards the treated tissue. A central electrode 806 acts as a first plasma electrode, while a ring shaped electrode 807, acts as a second plasma electrode.

Preferably, ring shaped electrode 807 is placed on outside surface of tube 805. Preferably, central electrode 806 is covered with thin electrically insulating material. It was found that insulating the central electrode 806 improves plasma welding process and uniformity.

In a similar embodiment, central electrode 806 is missing. Optionally, outer electrode 807 is replaced with a coil for inductively exciting the plasma.

FIG. 13 schematically depicts a plasma head having a spiral central electrode 850 according to an exemplary embodiment of the current invention.

In contrast to previous embodiments, central electrode 806 of head 850 has a spiral shape. The spiral shape electrode creates magnetic field at center of the spiral, thus creating Inductive Coupled Plasma (ICP).

FIG. 14 schematically depicts an ergonometric plasma head 880 according to another embodiment of the current invention.

Ergonometric plasma head 880 is characterized by the bent or sectioned tube 881 having a distal plasma opening 882 at one end, and an ergonomic handle 883 at the other end. The ergonomic shape of plasma head 880 ease the manipulation of the head, may reduce strain and fatigue of the operator and may increase efficiency and speed of operation.

Plasma production may be according to any of the embodiments disclosed herein.

FIG. 15 schematically depicts a plasma head 900 having stand-off legs 905 for controlling the distance of the plasma head to the treated tissue.

Plasma head 900 receives RF power and gas supply via hose 901 connected to the body 902 at the proximal end of the body 902. The body 902 shaped to be hand held and to be manipulated by the user. The plasma head 900 further comprises a plasma tube 904 near the distal end of the body 902. Plasma is generated at the plasma tube 904 and exits toward the cut 260 in the patient's skin 906. To assist the user in keeping the opening of plasma tube 804 at the correct distance from the skin 906, at least one, and preferably two stand-off legs 905 protrude from the body 902 of head 900. By resting the legs 905 against the skin 906, proper distance is easily maintained.

FIG. 16 schematically depicts a wiper 950 for uniformly spreading albumin solution on tissue according to another embodiment of the current invention.

Wiper 950 comprises a handle 951 constructed to be hand held and preferably ergonomically shaped, for example in may be bent for ease of manipulation, have finger grips or covered with non-slip material. At the distal end, a wiper member 952 is attached. Wiper member 952 is preferably made of thin elastic material such as silicon rubber or other soft material and is used for uniformly spreading albumin solution applied to a tissue or a cut in the tissue or skin.

Optionally, an indentation 954 in the edge 953 of the wiper member 952 help in leaving the desired among of albumin solution, while wiping off excess albumin. For example, and without limitation, the indentation in the blade id 0.6 mm deep and 6 mm wide.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A medical device for tissue welding comprising:
   a conduit, capable of transferring gas from a gas handling sub-system and RF signal from an RF circuit to a hand-held plasma head; and
   a plasma head for a hand-held applicator, said plasma head configured to support a tip comprising:
   a plasma tube having a proximal opening and a distal opening, the tube being configured to receive said gas through the proximal opening and to provide gas to a plasma region through the distal opening; and
   plasma exciter configured to excite gas and thereby generate plasma in said plasma region,
   wherein the device further comprises a controller, said controller being configured to receive user input and a plasma feedback signal and to adjust operation of at least one of: a gas handling sub-system and an RF circuit in response to said user input and plasma feedback signal and said RF circuit further comprises a plasma spectroscope, and wherein the controller is further configured to generate said feedback signal by measuring an emission spectra of said plasma.

2. The medical device of claim 1 further comprising an optical fiber for collecting plasma emission radiation at a distal end thereof, which is located proximate to said plasma tube and is further configured to transfer said radiation to said spectrometer.

3. The medical device of claim 1 wherein the controller is further configured to generate said feedback signal by measuring said tissue temperature using an IR sensor.

4. A medical device for tissue welding comprising:
   a conduit, capable of transferring gas from a gas handling sub-system and RF signal from an RF circuit to a hand-held plasma head; and
   a plasma head for a hand-held applicator, said plasma head configured to support a tip comprising:
   a plasma tube having a proximal opening and a distal opening, the tube being configured to receive said gas through the proximal opening and to provide gas to a plasma region through the distal opening; and
   plasma exciter configured to excite gas and thereby generate plasma in said plasma region,
   wherein said plasma exciter comprises a ring electrode external to said plasma tube and an electrode internal to said plasma tube and wherein said electrode internal to said plasma tube is covered with an electrical insulation layer.

5. A medical device for tissue welding comprising:
   a conduit, capable of transferring gas from a gas handling sub-system and RF signal from an RF circuit to a hand-held plasma head; and
   a plasma head for a hand-held applicator, said plasma head configured to support a tip comprising:
   a plasma tube having a proximal opening and a distal opening, the tube being configured to receive said gas through the proximal opening and to provide gas to a plasma region through the distal opening; and
   plasma exciter configured to excite gas and thereby generate plasma in said plasma region, wherein said plasma exciter comprises a ring electrode external to said plasma tube and an electrode internal to said plasma tube and wherein said electrode internal to said plasma tube has helical shape.

6. A plasma treatment device comprising:
an applicator head;
a gas flow chamber associated with the applicator head, the gas flow chamber configured to support plasma formation;
a gas conduit for delivering gas to the gas flow chamber; and
a radio frequency exciter substantially surrounding a periphery of the gas flow chamber,
the radio frequency exciter configured to ignite a plasma in the gas flow chamber when gas is delivered to the plasma formation zone via the conduit, wherein the radio frequency exciter is a wire coil.

7. The plasma treatment device of claim 6, wherein the radio frequency exciter band is a metal ring.

8. The plasma treatment device of claim 6, further comprising an electrically insulating material, substantially separating the exciter from the plasma.

9. The plasma treatment device of claim 6, wherein the exciter is located proximate an opening of the gas flow chamber.

10. The plasma treatment device of claim 6, wherein the gas flow chamber has an elongated shape with a length at least four times its width.

11. The plasma treatment device of claim 6, wherein the exciter is configured to substantially uniformly deliver energy to the gas.

* * * * *